United States Patent [19]

Dubs et al.

[11] Patent Number: 5,668,206

[45] Date of Patent: Sep. 16, 1997

[54] LIQUID ANTIOXIDANTS AS STABILIZERS

[75] Inventors: Paul Dubs, Marly; Roger Martin, Fribourg; Samuel Evans, Marly, all of Switzerland

[73] Assignee: Ciba-Geigy Corporation, Tarrytown, N.Y.

[21] Appl. No.: 466,520

[22] Filed: Jun. 6, 1995

Related U.S. Application Data

[62] Division of Ser. No. 41,664, Apr. 1, 1993, Pat. No. 5,478,875.

[30] Foreign Application Priority Data

Apr. 8, 1992 [CH] Switzerland ............................. 1153/92

[51] Int. Cl.$^6$ ............................. C08K 5/04; C08K 5/06; C08K 5/10

[52] U.S. Cl. ............................. 524/291; 524/289; 524/334; 524/366; 524/367; 524/368; 524/379; 524/386

[58] Field of Search ............................. 524/289, 291, 524/334, 379, 386, 366

[56] References Cited

U.S. PATENT DOCUMENTS

| | | | |
|---|---|---|---|
| 3,330,859 | 7/1967 | Dexter et al. | 560/75 |
| 3,839,278 | 10/1974 | Dexter et al. | 524/291 |
| 3,944,594 | 3/1976 | Kleiner et al. | 524/291 |
| 3,960,928 | 6/1976 | Mauz | 560/75 |
| 4,032,562 | 6/1977 | Dexter et al. | 560/75 |
| 4,058,502 | 11/1977 | Dexter et al. | 524/289 |
| 4,093,587 | 6/1978 | Spivack | 524/222 |
| 4,132,702 | 1/1979 | Schmidt et al. | 524/84 |
| 4,325,863 | 4/1982 | Hinsken et al. | 524/111 |
| 4,338,244 | 7/1982 | Hinsken et al. | 524/109 |
| 4,544,694 | 10/1985 | Bower | 524/386 |
| 4,593,057 | 6/1986 | Stephen | 524/291 |
| 4,598,113 | 7/1986 | Stephen et al. | 524/291 |
| 4,603,159 | 7/1986 | Ishii et al. | 524/291 |
| 5,155,244 | 10/1992 | Greene et al. | 560/75 |

FOREIGN PATENT DOCUMENTS

| | | |
|---|---|---|
| 0154518 | 8/1985 | European Pat. Off. |
| 996502 | 6/1965 | United Kingdom |
| WO9113134 | 9/1991 | WIPO |

OTHER PUBLICATIONS

G. Abellaneda et al. 3rd. Symposium CEC (1989) London, 61, New Cavendish St. Wim 8AR, England.

*Primary Examiner*—Tae Yoon
*Attorney, Agent, or Firm*—Luther A. R. Hall

[57] ABSTRACT

Products are described which can be obtained by reacting components a), b) and c), where component a) is a compound of the formula I or a mixture of compounds of the formula I, component b) is a compound of the formula II or a mixture of compounds of the formula II and component c) is a compound of the formula III or a mixture of compounds of the formula III, $$X(Y)_a \quad (I)$$

$$\begin{array}{c} CH_2\text{—}OZ \\ | \\ (CH_2\text{—}OZ)_k \\ | \\ CH_2\text{—}OZ \end{array} \quad (II)$$

$$\left( \text{HO} \begin{array}{c} R_{12} \\ \diagup \\ (R_{15})_s \end{array} \text{—Q—C(=O)—O} \right)_n R_{17} \quad (III)$$

in which the general symbols are as defined in claim 1, the compound of the formula I being, for example, pentaerythritol, thiodiethylene glycol, 1,4-butanediol, 1,4-propanediol, diethylene glycol, triethylene glycol, diethanolamine or glycerol, the compound of the formula II being, for example, sunflower oil or coconut fat, and the compound of the formula III being, for example, methyl 3-(3',5'-di-tert-butyl-4'-hydroxyphenyl)propionate. The abovementioned products can be used as liquid antioxidants in polymers and lubricants.

15 Claims, No Drawings

LIQUID ANTIOXIDANTS AS STABILIZERS

This is a divisional of application Ser. No. 08/041,664, filed on Apr. 1, 1993, now U.S. Pat. No. 5,478,875, issued on Dec. 26, 1995.

The present invention relates to novel liquid antioxidants with low volatility, to compositions comprising an organic material, preferably a polymer or oil, as well as the novel, liquid antioxidants which have low volatility, and to their use for stabilising organic materials against oxidative, thermal or light-induced degradation.

The stabilisation, in particular of lubricants or of plastics, with antioxidants from the series of the sterically hindered phenols is known, for example, from U.S. Pat. Nos. 3,839,278, 4,032,562, 4,093,587 and 4,132,702.

WO 91/13134 describes a method for improving the solubility of antioxidants in a second medium.

The present invention relates to products which can be obtained by reacting components a), b) and c), where component a) is a compound of the formula I or a mixture of compounds of the formula I, component b) is a compound of the formula II or a mixture of compounds of the formula II and component c) is a compound of the formula III or a mixture of compounds of the formula III, $$X(Y)_a, \qquad (I)$$

$$\begin{array}{l} CH_2-OZ \\ | \\ (CH_2-OZ)_k, \\ | \\ CH_2-OZ \end{array} \qquad (II)$$

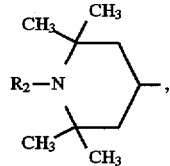  (III)

in which, in the compound of the formula I, the radicals Y independently of one another are OH, $(HOCH_2CH_2)_2N-$ or $-HNR_1$ and the radicals $R_1$ are hydrogen, $C_1-C_{18}$alkyl, $C_5-C_{12}$cycloalkyl,

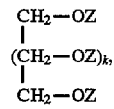

$C_3-C_6$alkenyl, $C_7-C_9$phenylalkyl, phenyl, or phenyl which is substituted by 1 to 3 radicals $A_1$, the radicals $A_1$ independently of one another being $C_1-C_{12}$alkyl, halogen, hydroxyl, methoxy or ethoxy, in which $R_2$ is hydrogen, $C_1-C_8$alkyl, O•, OH, NO, $-CH_2CN$, $C_1-C_{18}$alkoxy, $C_5-C_{12}$cycloalkoxy, $C_3-C_6$alkenyl, $C_7-C_9$phenylalkyl or $C_7-C_9$phenylalkyl which is mono-, di- or trisubstituted on the phenyl ring by $C_1-C_4$alkyl, or $R_2$ is furthermore $C_1-C_8$acyl or $HOCH_2CH_2$, and a is the number 1, 2, 3, 4 or 6, where, if Y is OH and a is 1, X is $C_1-C_{45}$alkyl, $C_3-C_{18}$alkenyl, $-CH_2CH_2T_1$ $(CH_2CH_2O)_bR_4$ or

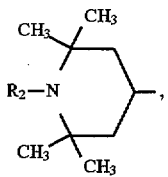

in which $R_2$ is as defined above, and $T_1$ is oxygen, sulfur or

$R_4$ is $C_1-C_{20}$alkyl, b is an integer ranging from 0 to 10 and $R_5$ is hydrogen, $C_1-C_{18}$alkyl or phenyl, or, if Y is OH and a is 2, X is $-CH_2CH_2T_2(CH_2CH_2O)_bCH_2CH_2-$, in which b is as defined above,

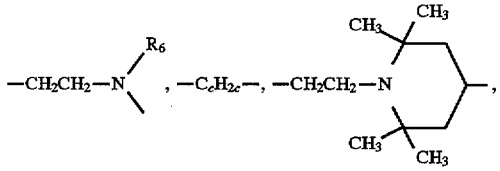

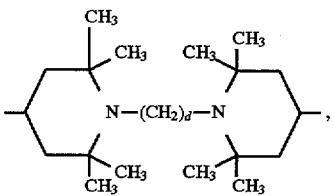

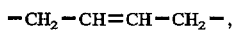

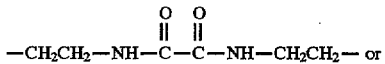

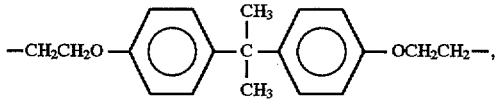

in which $T_2$ is oxygen, sulfur,

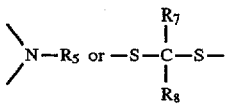

and $R_5$ is as defined above, $R_6$ is hydrogen, $C_1-C_{18}$alkyl or phenyl, c is an integer ranging from 2 to 10, d is an integer ranging from 2 to 6 and $R_7$ and $R_8$ independently of one another are hydrogen, $C_1-C_{18}$alkyl or phenyl, or $R_7$ and $R_8$ together with the C atom to which they are bonded form a $C_5-C_{12}$cycloalkyl ring, or, if a is 3, X is $C_3$–$C_{10}$alkanetriyl or $N(CH_2CH_2\text{—})_3$, or if Y is OH and a is 4, X is $C_4$–$C_{10}$alkanetetrayl,

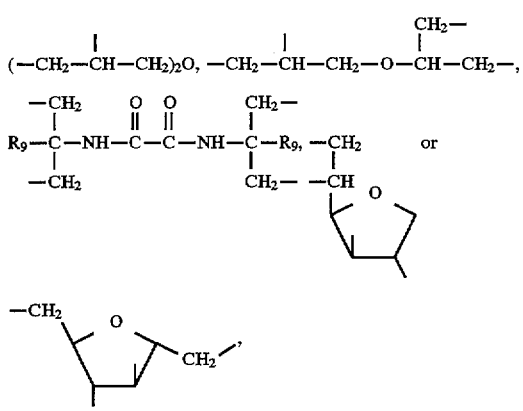

in which $R_9$ is $C_1$–$C_4$alkyl, or, if Y is OH and a is 6,

X is

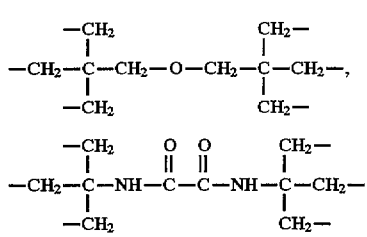

or $C_6$–$C_{10}$alkanehexayl, or if Y is $HNR_1$ and a is 1,

X is $C_1$–$C_{18}$alkyl, $C_3$–$C_{18}$alkenyl, $C_5$–$C_{12}$cycloalkyl, $C_7$–$C_9$phenylalkyl, phenyl,

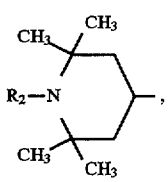

in which $R_2$ is as defined above or X is furthermore

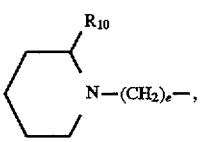

or X together with $R_1$ is a group of the formula $\text{—CH}_2\text{CH}_2\text{CH}_2\text{CH}_2\text{CH}_2\text{—}$ or $\text{—CH}_2\text{CH}_2\text{OCH}_2\text{CH}_2\text{—}$, in which $R_{10}$ is hydrogen or methyl and e is 2 or 3, or, if Y is $\text{—HNR}_1$ and a is 2, X is

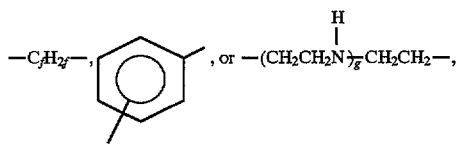

in which f is an integer ranging from 2 to 10 and g is an integer ranging from 1 to 6, and, in the compound of the formula II, the radicals Z are hydrogen or a group of the formula

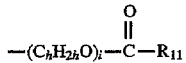

and k is an integer ranging from 0 to 6, in which h is 2 or 3, i is an integer ranging from 0 to 12 and $R_{11}$ is $C_1$–$C_{30}$alkyl, $C_8$–$C_{30}$alkenyl, $C_5$–$C_{12}$cycloalkyl, phenyl or $C_7$–$C_9$phenylalkyl, with the proviso that the compound of the formula II has a group

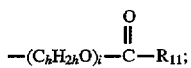

in the compound of the formula III, $R_{12}$ is $C_1$–$C_{18}$alkyl, $C_5$–$C_{12}$cycloalkyl, phenyl or $C_7$–$C_9$phenylalkyl, $R_{15}$ is hydrogen, $C_1$–$C_{18}$alkyl, $C_5$–$C_{12}$cycloalkyl, phenyl or $C_7$–$C_9$phenylalkyl, s is 0, 1 or 2, Q is

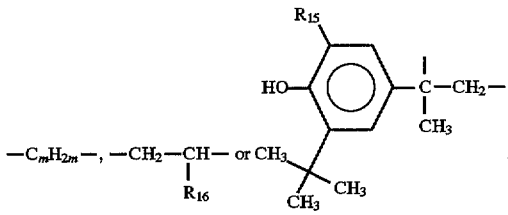

in which $R_{15}$ is as defined above, m is an integer ranging from 0 to 3, $R_{16}$ is $C_1$–$C_8$alkyl and n is an integer ranging from 1 to 6, where, if n is 1, $R_{17}$ is hydrogen, $C_1$–$C_{45}$alkyl, $C_5$–$C_{12}$cycloalkyl, $C_2$–$C_{18}$alkenyl, a monovalent radical of a hexose, a monovalent radical of a hexitol,

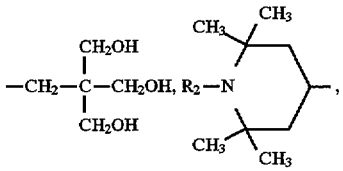

in which $R_2$ is as defined above, or furthermore $R_{17}$ is
—$CH_2CH_2$—$T_3$—$R_{19}$ or

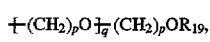

in which $T_3$ is oxygen, sulfur or

$R_{19}$ is

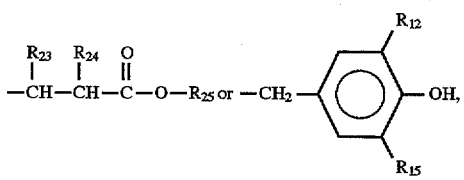

in which $R_{12}$ and $R_{15}$ are as defined above, or $R_{19}$ is furthermore hydrogen, $C_1$-$C_{24}$alkyl, phenyl, $C_5$-$C_{12}$cycloalkyl or

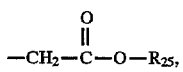

in which p is an integer ranging from 2 to 4.

q is an integer ranging from 2 to 20.

$R_{22}$ is $C_1$-$C_{18}$alkyl, phenyl or phenyl which is substituted by 1 to 3 radicals $A_1$, in which the radicals $A_1$ independently of one another are $C_1$-$C_{12}$alkyl, halogen, hydroxyl, methoxy or ethoxy, or $R_{22}$ is furthermore $C_5$-$C_8$cycloalkyl, $R_{23}$ and $R_{24}$ independently of one another are hydrogen or methyl with the proviso that $R_{23}$ and $R_{24}$ are not simultaneously methyl;

$R_{25}$ is hydrogen or $C_1$-$C_{24}$alkyl, or, if n is 2, $R_{17}$ is a divalent radical of a hexose, a divalent radical of a hexitol,

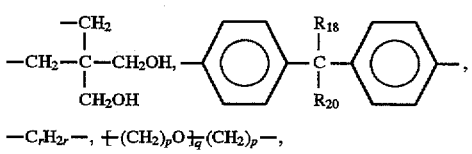

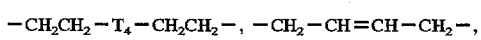

in which p and q are as defined above,

—$CH_2CH_2$—$T_4$—$CH_2CH_2$—, —$CH_2$—$CH$=$CH$—$CH_2$—,

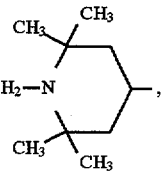

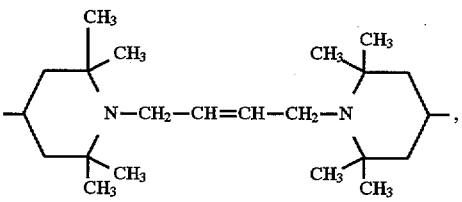

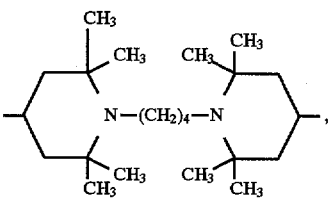

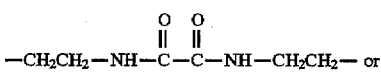

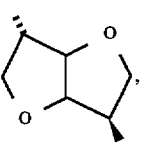

in which $R_{18}$ and $R_{20}$ independently of one another are hydrogen or $C_1$-$C_{12}$alkyl or together are the radical —$CH_2CH_2CH_2CH_2CH_2$—, r is an integer ranging from 2 to 10, $T_4$ is sulfur,

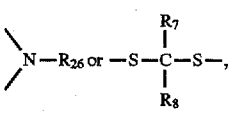

in which $R_7$ and $R_8$ are as defined above, and $R_{26}$ is hydrogen, $C_1$-$C_{18}$alkyl, phenyl phenyl which is substituted by 1 to 3 radicals $A_1$, in which the radicals $A_1$ are as defined above in formula I, or $R_{26}$ is furthermore $C_5$-$C_8$cycloalkyl or

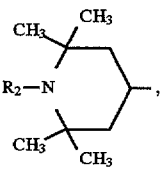

in which $R_2$ is as defined above, or, if n is 3, $R_{17}$ is a trivalent radical of a hexose, a trivalent radical of a hexitol,

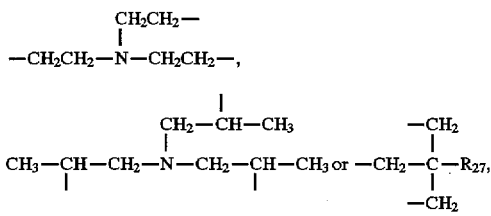

in which

R$_{27}$ is hydrogen, —CH$_2$OH, C$_1$–C$_4$alkyl, C$_1$–C$_{18}$alkylamido or

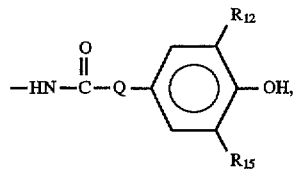

in which Q, R$_{12}$ and R$_{15}$ are as defined above, or, if n is 4,

R$_{17}$ is a tetravalent radical of a hexose, a tetravalent radical of a hexitol, C$_4$–C$_{10}$alkanetetrayl,

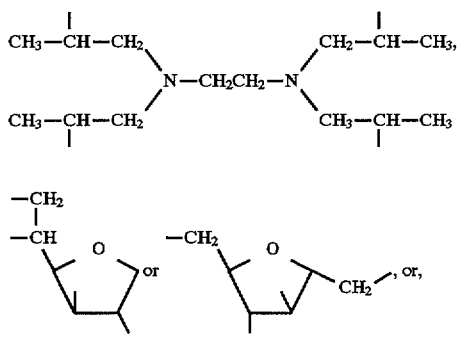

if n is 5,

R$_{17}$ is a pentavalent radical of a hexose or a pentavalent radical of a hexitol, or, if n is 6, R$_{17}$ is a hexavalent radical of a hexitol or

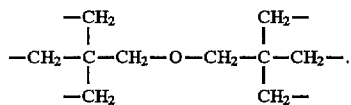

The liquid products of the present invention, which have low volatility, are distinguished by a very good stabilising action of organic materials, for example polymers or oils, and against oxidative, thermal and light-induced degradation.

Alkyl having not more than 45 C atoms is a branched or unbranched radical such as, for example, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl or pentacosyl. One of the preferred meanings of R$_1$, R$_4$ and R$_{16}$ is, for example, C$_{C4}$alkyl, of R$_2$ methyl, of R$_{11}$ C$_1$–C$_2$alkyl, of R$_{12}$ and R$_{15}$ C$_1$–C$_4$alkyl, in particular tert-butyl, and of R$_{17}$ C$_1$–C$_{18}$alkyl.

Cycloalkyl having not more than 12 C atoms is, for example, cyclopentyl, cyclohexyl, cycloheptyl, cyclooctyl, cyclodecyl or cyclododecyl. One of the preferred meanings of R$_1$, R$_{11}$, R$_{12}$ and R$_{15}$ is C$_5$–C$_7$cycloalkyl. Cyclohexyl is particularly preferred.

Alkenyl having not more than 30 C atoms is, for example, vinyl, propenyl, isopropenyl, 2-butenyl, 3-butenyl, isobutenyl, n-penta-2,4-dienyl, 3-methylbut-2-enyl, n-oct-2-enyl, n-dodec-2-enyl, iso-dodecenyl, oleyl, n-octadec-2-enyl or n-octadec-4-enyl. If R$_1$, R$_2$ and X are C$_3$–C$_6$alkenyl, then the C atom which is bonded to the nitrogen is advantageously saturated.

Phenylalkyl having 7 to 9 C atoms is, for example, benzyl, α-methylbenzyl, α,α-dimethylbenzyl or phenylethyl. Benzyl is preferred.

Examples of phenyl which is substituted by 1 to 3 radicals A$_1$ are o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 2-methyl-4-tert-butylphenyl, 2-ethylphenyl, 2,6-diethylphenyl, 2,6-diethyl-4-methylphenyl, 2,6-diisopropylphenyl, 4-tert-butylphenyl, p-nonylphenyl, o-, m- or p-chlorophenyl, 2,3-dichlorophenyl, 2,4-dichlorophenyl, 2,5-dichlorophenyl, 2,6-dichlorophenyl, 3,4-dichlorophenyl, 2,4,5-trichlorophenyl, 2,4,6-trichlorophenyl, o-, m- or p-hydroxyphenyl, o-, m- or p-methoxyphenyl, o- or p-ethoxyphenyl, 2,4-dimethoxyphenyl, 2,5-dimethoxyphenyl, 2,5-diethoxyphenyl, o-, m- or p-methoxycarbonyl, 2-chloro-6-methylphenyl, 3-chloro-2-methylphenyl, 3-chloro-4-methylphenyl, 4-chloro-2-methylphenyl, 5-chloro-2-methylphenyl, 2,6-dichloro-3-methylphenyl, 2-hydroxy-4-methylphenyl, 3-hydroxy-4-methylphenyl, 2-methoxy-5-methylphenyl, 4-methoxy-2-methylphenyl, 3-chloro-4-methoxyphenyl, 3-chloro-6-methoxyphenyl, 3-chloro-4,6-dimethoxyphenyl and 4-chloro-2,5-dimethoxyphenyl. Preferred is phenyl which is substituted by 1 or 2, in particular 1, radical(s) A$_1$, A$_1$ being, in particular, alkyl.

Alkyl having 1 to 18 C atoms is, for example, methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. One of the preferred meanings of R$_2$ is C$_6$–C$_{12}$alkoxy. Heptoxy and octoxy are particularly preferred.

Cycloalkoxy having 5 to 12 C atoms is, for example, cyclopentoxy, cyclohexoxy, cycloheptoxy, cyclooctoxy, cyclodecyloxy or cyclododecyloxy. One of the preferred meanings of R$_2$ is C$_5$–C$_8$cycloalkoxy. Cyclopentoxy and cyclohexoxy are particularly preferred.

Examples of C$_7$–C$_9$phenylalkyl which is mono-, di- or trisubstituted on the phenyl ring by C$_1$–C$_4$alkyl are methylbenzyl, dimethylbenzyl, trimethylbenzyl or tert-butylbenzyl.

Acyl having 1 to 8 C atoms is, for example, Formyl, Acetyl, Propionyl, Butyryl, Pentanoyl, Hexanoyl, Heptanoyl, Octanoyl, Benzoyl, Acryloyl or Crotonyl. C$_1$–C$_8$Alkanoyl, C$_3$–C$_8$alkenoyl or benzoyl, in particular acetyl, are preferred.

Alkanetriyl having 3 to 10 C atoms is, for example,

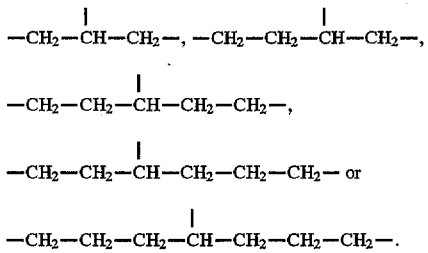

Glyceryl is preferred.

Alkanetetrayl having 4 to 10 C atoms is, for example,

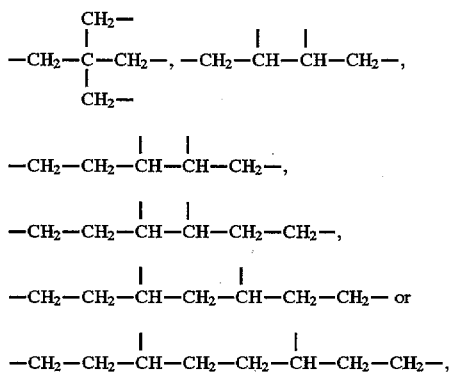

Pentaerythrityl is preferred.

Alkanehexayl having 6 to 10 C atoms is, for example,

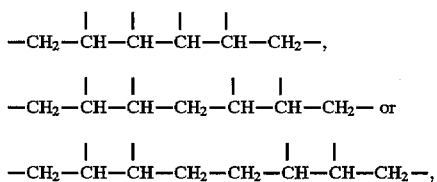

If $R_{17}$ with n=1 to 6 is an n-valent radical of a hexose, then this radical is derived, for example, from allose, altrose, glucose, mannose, gulose, idose, galactose or talose, i.e. to obtain the corresponding compounds of the formula III, one, two, three, four, five or six —OH groups must be replaced by the ester group E-1,

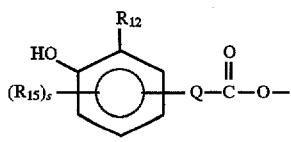
(E-1)

in which $R_{12}$, $R_{15}$, s and Q are as defined above. For example, $R_{17}$ with n=5 can be a group

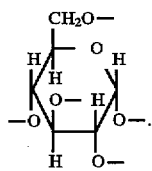

If $R_{17}$ is the n-valent radical of a hexitol, then the corresponding compounds of the formula III are obtained by replacing n —OH groups by the abovementioned ester group E-1. $R_{17}$ as a hexavalent radical of a hexitol can be, for example,

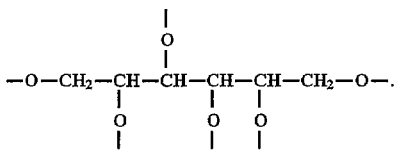

This group is derived from D-sorbitol.

Alkylamido having 1 to 18 C atoms is, for example, $CH_3$—CO—NH—, $CH_3CH_2$—CO—NH—, $C_6H_{13}$—CO—NH— or $C_{18}H_{37}$—CO—NH—.

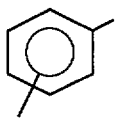

means that the phenyl ring can be ortho-, meta- or para-substituted.

The three components a), b) and c) can be reacted with each other to give the products of the present invention in any desired sequence.

Preferably, component a) is fast reacted with component b), and component c) is then added.

The reaction is advantageously carried out in the presence of a catalyst. Suitable catalysts are Lewis acids or bases.

Examples of suitable basic catalysts are metal hydrides, metal alkylides, metal arylides, metal hydroxides, metal alcoholales, metal phenolales, metal amides or metal carboxylates.

Examples of preferred metal hydrides are lithium hydride, sodium hydride or potassium hydride.

Examples of preferred metal alkylides are butyllithium or methyllithium.

An example of a preferred metal arylide is phenyllithium.

Examples of preferred metal hydroxides are lithium hydroxide, sodium hydroxide, potassium hydroxide, caesium hydroxide, rubidium hydroxide, magnesium hydroxide, calcium hydroxide, barium hydroxide or alurainium hydroxide.

Examples of preferred metal alcoholales are sodium methanolate, sodium ethanolate, potassium methanolate, potassium ethanolate, sodium isopropylate or potassium tert-butylate.

Examples of preferred metal phenolates are sodium phenolate or potassium phenolate.

Examples of preferred metal amides are sodium amide or lithium amide.

An example of a preferred metal carboxylate is calcium acetate.

Examples of suitable Lewis acid catalysts are or

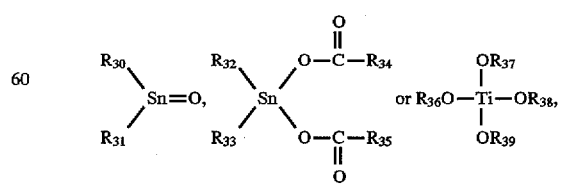

the radicals $R_{30}$, $R_{31}$, $R_{32}$, $R_{33}$, $R_{34}$, $R_{35}$, $R_{36}$, $R_{37}$, $R_{38}$ and $R_{39}$ being, independently of one another, for example $C_1$–$C_{18}$alkyl or phenyl. $C_1$–$C_8$Alkyl is preferred. A particularly preferred Lewis acid catalyst is dibutyltin oxide.

The catalyst is added to components a), b) and c) for example in an amount of from 0.05 to 10 per mil by weight, preferably in an amount of from 0.1 to 5 per mil by weight. An addition of 1 to 2 per mil by weight of dibutyltin oxide is particularly preferred.

The components a), b) and c) can be reacted in a solvent, for example xylene, or without solvent. The reaction is preferably carried out without solvent.

The reaction temperature is, for example, between 130° and 250° C. The reaction is preferably carried out in a temperature range from 130° to 190° C.

The application also relates to a process for the preparation of the products according to the invention, which comprises reacting the components a), b) and c) in a molar quantitative ratio of 0.1:1:0.1 to 15:1:30.

If components a), b) and c) are not commercially available, they can be prepared by known processes or analogously. Possible preparation processes for the compounds of the formula III can be found, for example, in the following publications: GB-A-996 502, U.S. Pat. Nos. 3,330,859, 3,944,594, 4,593,057, EP-A-154 518 or U.S. Pat. No. 3,960,928.

The invention preferably relates to products where, in the compound of the formula III, s is the number 1 or 2.

The invention also preferably relates to products in which, in the compound of the formula I, the radicals Y independently of one another are OH, $(HOCH_2CH_2)_2N$— or —$HNR_1$ and $R_1$ is hydrogen, $C_1$–$C_{10}$alkyl, $C_5$–$C_7$cycloalkyl,

[structure: 2,2,6,6-tetramethylpiperidine with $R_2$–N]

$C_3$–$C_6$alkenyl, benzyl or phenyl, in which $R_2$ is hydrogen, $C_1$–$C_4$alkyl, OH, $CH_2CN$, $C_6$–$C_2$alkoxy, $C_5$–$C_8$cycloalkoxy, allyl, benzyl, acetyl or $HOCH_2CH_2$— and a is the number 1,2,3,4 or 6, where, if Y is OH and a is 1, X is $C_1$–$C_{30}$alkyl, $C_3$–$C_{18}$alkenyl, —$CH_2CH_2T_1$ $(CH_2CH_2O)_bR_4$ or

[structure: 2,2,6,6-tetramethylpiperidine with $R_2$–N]

in which $R_2$ is as defined above, and $T_1$ is oxygen, sulfur or $\diagdown\!\!\!\!\!\diagup$ N—$R_5$, $R_4$ is $C_1$–$C_{10}$alkyl, b is an integer ranging from 0 to 10 and $R_5$ is hydrogen, $C_1$–$C_{10}$alkyl or phenyl, or, if Y is OH and a is 2, X is —$CH_2CH_2T_2(CH_2CH_2O)_bCH_2CH_2$—, in which b is as defined above,

[structures: —$CH_2CH_2$—N with $R_6$; —$C_cH_{2c}$—; —$CH_2CH_2$—N(tetramethylpiperidine)]

[structure: bis(tetramethylpiperidine) linked by N—$(CH_2)_d$—N]

—$CH_2$—CH=CH—$CH_2$—, $$—CH_2CH_2—NH—\underset{\underset{O}{\|}}{C}—\underset{\underset{O}{\|}}{C}—NH—CH_2CH_2—\text{ or}$$

[structure: —$CH_2CH_2O$—phenyl—C(CH$_3$)$_2$—phenyl—$OCH_2CH_2$—]

$T_2$ is oxygen, sulfur, $$\diagdown\!\!\!\!\!\diagup\text{N}—R_5 \text{ or } —S—\underset{\underset{R_8}{|}}{\overset{\overset{R_7}{|}}{C}}—S—$$

and $R_5$ is as defined above, $R_6$ is hydrogen, $C_1$–$C_{10}$alkyl or phenyl, c is an integer ranging from 2 to 10, d is an integer ranging from 2 to 6 and $R_7$ and $R_8$ independently of one another are hydrogen, $C_1$–$C_{10}$alkyl or phenyl, or $R_7$ and $R_8$ together with the C atom to which they are bonded form a $C_5$–$C_7$cycloalkyl ring, or, if Y is —$HNR_1$ and a is 1, X is $C_1$–$C_{10}$alkyl, $C_3$–$C_{18}$alkenyl, $C_4$–$C_7$cycloalkyl, benzyl, phenyl,

[structure: 2,2,6,6-tetramethylpiperidine with $R_2$–N]

in which $R_2$ is as defined above, or X is furthermore

[structure: piperidine N—$(CH_2)_e$— with $R_{10}$]

or X together with $R_1$ is a group of the formula —$CH_2CH_2CH_2CH_2CH_2$— or —$CH_2CH_2OCH_2CH_2$—, in which $R_{10}$ is hydrogen or methyl and e is 2 or 3, and in the compound of the formula II, the radicals Z are hydrogen or a group of the formula

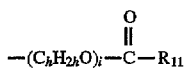

and k is an integer ranging from 0 to 4, in which h is 2 or 3, i is an integer ranging from 0 to 6 and $R_{11}$ is $C_1$-$C_{20}$alkyl, $C_8$-$C_{20}$alkenyl, $C_5$-$C_7$cycloalkyl, phenyl or benzyl, with the proviso that the compound of the formula II comprises a group

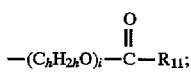

in the compound of the formula III $R_{12}$ is $C_1$-$C_6$alkyl, $C_5$-$C_7$cycloalkyl, phenyl or benzyl $R_{15}$ is is hydrogen, $C_1$-$C_6$alkyl, $C_5$-$C_7$cycloalkyl, phenyl or benzyl, s is 1 or 2, Q is

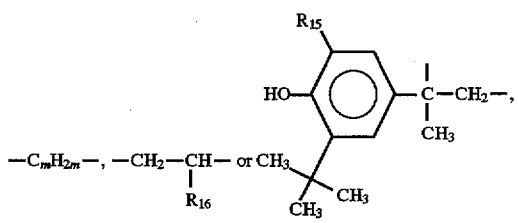

in which $R_{15}$ is as defined above, m is an integer ranging from 0 to 3, $R_{16}$ is $C_1$-$C_4$alkyl and n is an integer ranging from 1 to 6, where, if n is 1, $R_{17}$ is hydrogen, $C_1$-$C_{30}$alkyl, $C_5$-$C_7$cycloalkyl, $C_2$-$C_{18}$alkenyl, a monovalent radical of a hexose, a monovalent radical of a hexitol,

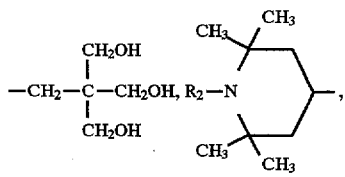

in which $R_2$ is as defined above, or furthermore $R_{17}$ is —$CH_2CH_2$—$T_3$—$R_{19}$ or

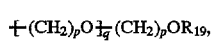

in which $T_3$ is oxygen, sulfur or

$R_{19}$ is

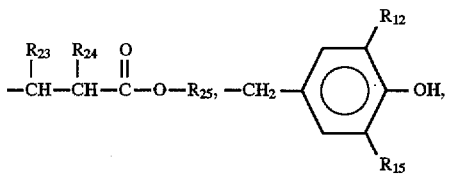

in which $R_{12}$ and $R_{15}$ are as defined above, or $R_{19}$ is furthermore hydrogen, $C_1$-$C_{18}$alkyl, phenyl, $C_5$-$C_7$cycloalkyl or

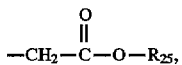

in which p is an integer ranging from 2 to 4, q is an integer ranging from 2 to 20, $R_{22}$ is $C_1$-$C_{10}$alkyl, phenyl or $C_5$-$C_8$acycloalkyl, $R_{23}$ and $R_{24}$ independently of one another are hydrogen or methyl with the proviso that $R_{23}$ and $R_{24}$ are not simultaneously methyl;

$R_{25}$ is hydrogen or $C_1$-$C_{18}$alkyl, or, if n is 2, $R_{17}$ is a divalent radical of a hexose, a divalent radical of a hexitol,

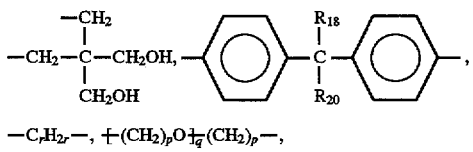

in which p and q are as defined above

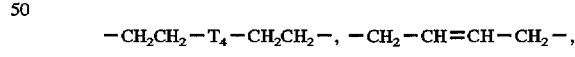

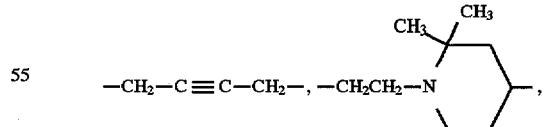

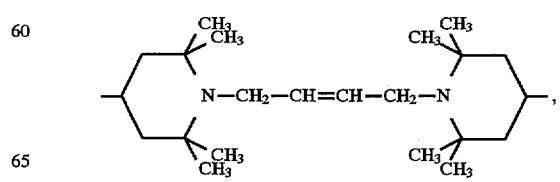

-continued

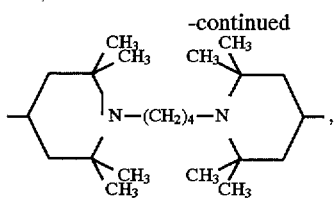

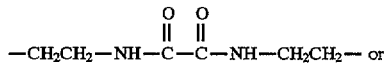

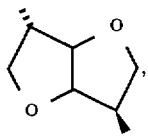

in which

R$_{18}$ and R$_{20}$ independently of one another are hydrogen or C$_1$–C$_6$alkyl or together are the radical —CH$_2$CH$_2$CH$_2$CH$_2$CH$_2$—, r is an integer ranging from 2 to 10, T$_4$ is sulfur,

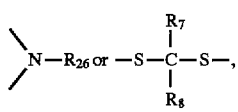

in which R$_7$ and R$_8$ are as defined above and

R$_{26}$ is hydrogen, C$_1$–C$_{10}$alkyl, phenyl, C$_5$–C$_8$cycloalkyl or

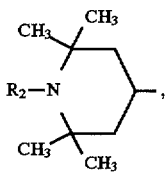

in which R$_2$ is as defined above.

The invention particularly preferably relates to products in which, in the compound of the formula I, the radicals Y independently of one another are OH, (HOCH$_2$CH$_2$)$_2$N— or —HNR$_1$ and R$_1$ is hydrogen, C$_1$–C$_4$alkyl or

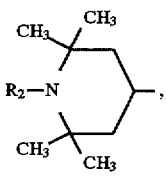

in which

R$_2$ is hydrogen, C$_1$–C$_4$alkyl, OH, allyl, benzyl, acetyl or HOCH$_2$CH$_2$— and a is the number 1,2,3,4 or 6, where if Y is OH and a is 1, X is C$_1$–C$_{18}$alkyl, C$_3$–C$_{18}$alkenyl, —CH$_2$CH$_2$T$_1$ (CH$_2$CH$_2$O)$_b$R$_4$ or

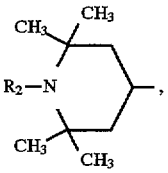

in which R$_2$ is as defined above, and

T$_1$ is oxygen,

R$_4$ is C$_1$–C$_4$alkyl and b is an integer ranging from 0 to 10, or if Y is OH and a is 2, X is —CH$_2$CH$_2$T$_2$(CH$_2$CH$_2$O)$_b$CH$_2$CH$_2$—, in which b is as defined above, or furthermore X is

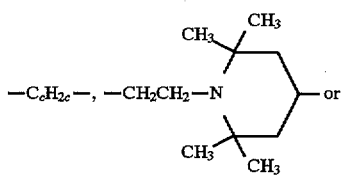

—CH$_2$—CH=CH—CH$_2$—, in which

T$_2$ is oxygen, sulfur or

R$_5$ is hydrogen, b is the number 0 or 1 and c is an integer ranging from 2 to 8, or, if a is 3, X is

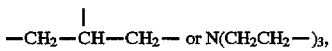

or if Y is OH and a is 4,

X is

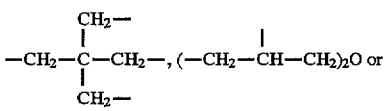

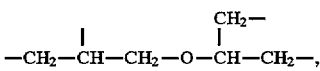

or if Y is OH and a is 6,

X is

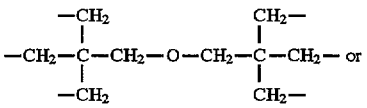

-continued

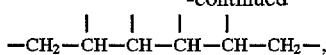

or, if Y is —HNR$_1$ and a is 1,

X is C$_1$–C$_{10}$alkyl, C$_3$–C$_{18}$alkenyl, C$_5$–C$_7$cycloalkyl or

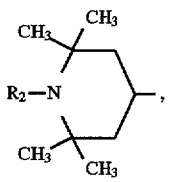

where R$_2$ is as defined above, or, if Y is —HNR$_1$ and a is 2,

X is —C$_f$H$_{2f}$— in which f is an integer ranging from 2 to 10 and, in the compound of the formula II, the radicals Z are hydrogen or a group of the formula

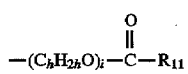

and k is 1,2 or 3, h is 2 or 3, i is an integer ranging from 0 to 4 and

R$_{11}$ is C$_1$–C$_{20}$alkyl or C$_8$–C$_{20}$alkenyl, with the proviso that the compound of the formula II comprises a group

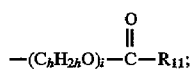

in the compound of the formula III,

R$_{12}$ is C$_1$–C$_6$alkyl or C$_5$–C$_7$cycloalkyl,

R$_{15}$ is hydrogen, C$_1$–C$_6$alkyl or C$_5$–C$_7$cycloalkyl, s is 1 or 2,

Q is —C$_m$H$_{2m}$— or

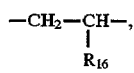

m is an integer ranging from 0 to 3,

R$_{16}$ is C$_1$–C$_4$alkyl and n is an integer ranging from 1 to 6, where, if n is 1, R$_{17}$ is hydrogen, C$_1$–C$_{18}$alkyl, C$_5$–C$_7$cycloalkyl, C$_2$–C$_{18}$alkenyl, a monovalent radical of a hexose, a monovalent radical of a hexitol,

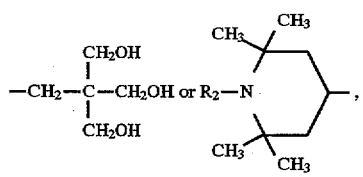

in which

R$_2$ is as defined above, or furthermore R$_{17}$ is

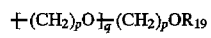

in which

R$_{19}$ is hydrogen, C$_1$–C$_{18}$alkyl or C$_5$–C$_7$cycloalkyl, in which p is an integer ranging from 2 to 4, q is an integer ranging from 2 to 10, or, if n is 2, R$_{17}$ is a divalent radical of a hexose, a divalent radical of a hexitol,

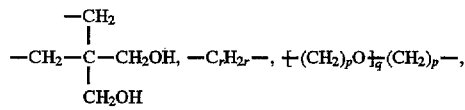

in which p and q are as defined above, —CH$_2$CH$_2$—T$_4$—CH$_2$—, or

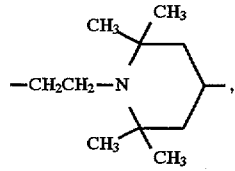

in which r is an integer ranging from 2 to 10,

T$_4$ is sulfur or

and

R$_{26}$ is hydrogen, C$_1$–C$_{10}$alkyl or C$_5$–C$_8$cycloalkyl, or, if n is 3, R$_{17}$ is a trivalent radical of a hexose, a trivalent radical of a hexitol,

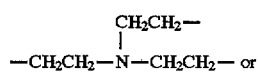

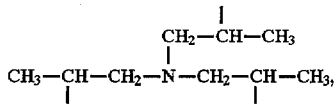

or, if n is 4,

R$_{17}$ is a tetravalent radical of a hexose, a tetravalent radical of a hexitol,

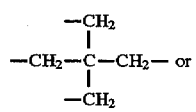

-continued

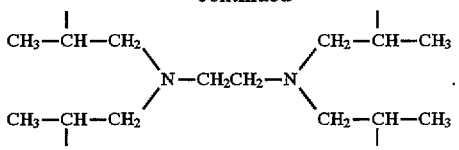

The invention furthermore preferably relates to products in which, in the compound of the formula I, the radicals Y independently of one another are hydroxyl or —NH$_2$ and a is an integer ranging from 1 to 4, where, if a is 1,
X is

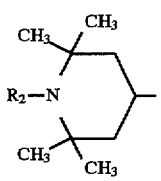

and

R$_2$ is hydrogen, methyl or HOCH$_2$CH$_2$—, or,
if Y is OH and a is 2,
X is —CH$_2$CH$_2$T$_2$(CH$_2$CH$_2$O)$_b$CH$_2$CH$_2$—,

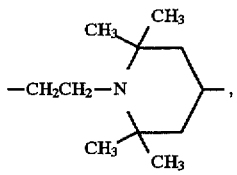

in which
T$_2$ is oxygen, sulfur or

R$_5$ is hydrogen,
b is the number 0 or 1 and
c is the number 2, 3 or 4, or,
if Y is OH and a is 3,
X is

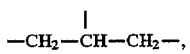

or,
if Y is OH and a is 4,
X is

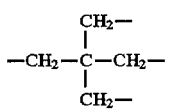

and, in the compound of the formula II, the radicals Z are hydrogen or a group of the formula

k is the number 1 and
R$_{11}$ is C$_1$–C$_{20}$alkyl or C$_8$–C$_{20}$alkenyl, with the proviso that the compound of the formula II comprises a group

and, in the compound of the formula III,
R$_{12}$ is tert-butyl,
R$_{15}$ is C$_1$–C$_4$alkyl and is bonded in the ortho-position relative to the OH group,
s is the number 1,
Q is —C$_m$H$_{2m}$— and is bonded in the para-position relative to the OH group, where m is the number 2,
n is 1 and
R$_{17}$ is C$_1$–C$_4$alkyl.

Examples of preferred compounds of the formula I are pentaerythritol, thiodiethylene glycol, 1,4-butanediol, 1,2-propanediol, diethylene glycol, triethylene glycol, diethanolamine, glycerol,

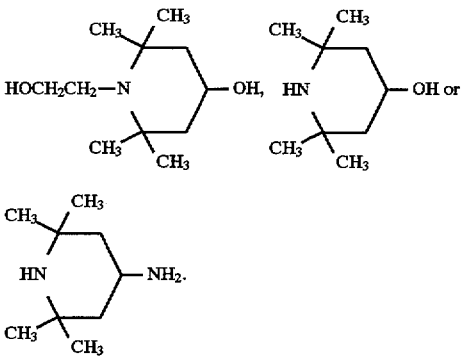

Glycerol or thiodiethylene glycol are particularly preferred. Preferred compounds of the formula II are naturally occurring vegetable oils, fats and waxes, animal oils and fats as well as artificial polyol derivatives. Preferred vegetable oils, fats and waxes are, for example, sunflower oil, coconut fat, rapeseed oil, soya oil, maize germ oil, safflower oil, olive oil, groundnut oil, cottonseed oil, sesame seed oil, castor oil, tallow oil, pumpkin seed oil or linseed oil.

Preferred animal oils and fats are, for example, butter fat, lard, fish oil, sperm oil, neat's foot oil or train oils.

Examples of preferred artificial polyol derivatives are Radiamuls (glycerol tri C$_8$/C$_{10}$) or sorbitan derivatives. The sorbitan derivatives are commercially available, for example, under the names Span®20, Span®40, Span®60, Span®65, Span®80, Span®85, Tween 20®, Tween 40®, Tween 60®, Tween 65®, Tween 80®or Tween 85®.

Sunflower oil, coconut fat or rapeseed oil are particularly preferred.

The invention furthermore preferably relates to products in which, in the compound of the formula III,
R$_{12}$ is C$_1$–C$_4$alkyl or cyclohexyl,
R$_{15}$ is C$_1$–C$_4$alkyl or cyclohexyl and is bonded in the ortho-position relative to the OH group,
s is the number 1, Q is —$C_mH_{2m}$— and is bonded in the para-position relative to the OH group, where
m is an integer ranging from 0 to 3 and
n is an integer ranging from 1 to 4, where,
if n is 1,
$R_{17}$ is hydrogen, $C_1$–$C_{10}$alkyl, cyclohexyl, $C_2$–$C_{18}$alkenyl or $$-CH_2-\underset{\underset{CH_2OH}{|}}{\overset{\overset{CH_2OH}{|}}{C}}-CH_2OH,$$

or if n is 2,
$R_{17}$ is $$-CH_2-\underset{\underset{CH_2OH}{|}}{\overset{\overset{-CH_2}{|}}{C}}-CH_2OH, \quad -C_rH_{2r}-, \quad +(CH_2)_pO\}_{\overline{q}}(CH_2)_p- \text{ or}$$

$$-CH_2CH_2-T_4-CH_2CH_2-$$

in which p is an integer ranging from 2 to 4,
q is an integer ranging from 2 to 10,
r is an integer ranging from 2 to 6,
$T_4$ is sulfur or $$\diagdown N-R_{26}$$
$$\diagup$$

and $R_{26}$ is hydrogen or $C_1$–$C_4$alkyl, or,
if n is 3,
$R_{17}$ is $$-CH_2CH_2-\underset{|}{N}-CH_2CH_2- \text{ or}$$
$$\overset{|}{CH_2CH_2-}$$

$$CH_3-CH-CH_2-\underset{|}{N}-CH_2-CH-CH_3,$$
$$\overset{|}{CH_2-CH-CH_3}$$

or, if n is 4,
$R_{17}$ is $$-CH_2-\underset{\underset{-CH_2}{|}}{\overset{\overset{-CH_2}{|}}{C}}-CH_2- \text{ or}$$

-continued $$CH_3-CH-CH_2 \diagdown \quad \diagup CH_2-CH-CH_3$$
$$\qquad \qquad N-CH_2CH_2-N$$
$$CH_3-CH-CH_2 \diagup \quad \diagdown CH_2-CH-CH_3$$

The invention furthermore particularly preferably relates to products in which in the compound of the formula III,
$R_{12}$ is tert-butyl,
$R_{15}$ is $C_1$–$C_4$alkyl and is bonded in the ortho-position relative to the OH group,
s is the number 1,
Q is —$C_mH_{2m}$— and is bonded in the para-position relative to the OH group, where
m is the number 2 and
n is an integer 1, 2 or 4, where,
if n is 1,
$R_{17}$ is $C_1$–$C_4$alkyl, or,
if n is 2,
$R_{17}$ is $$+(CH_2)_pO\}_{\overline{q}}(CH_2)_p-$$

or —$CH_2CH_2$—$T_4$—$CH_2CH_2$—, in which
p is the number 2,
q is the number 2 and
$T_4$ is sulfur, or,
if n is 4,
$R_{17}$ is $$-CH_2-\underset{\underset{-CH_2}{|}}{\overset{\overset{-CH_2}{|}}{C}}-CH_2-.$$

Other preferred compounds of the formula III are $$\underset{(CH_3)_3C}{\overset{(CH_3)_3C}{HO-\bigcirc-CH_2CH_2COOCH_3,}}$$

$$\left[\underset{(CH_3)_3C}{\overset{(CH_3)_3C}{HO-\bigcirc-CH_2CH_2-\overset{O}{\underset{\|}{C}}-O-CH_2}}\right]_4 C,$$

$$\left[\underset{(CH_3)_3C}{\overset{(CH_3)_3C}{HO-\bigcirc-CH_2CH_2-\overset{O}{\underset{\|}{C}}-O-CH_2CH_2-O-CH_2}}\right]_2,$$

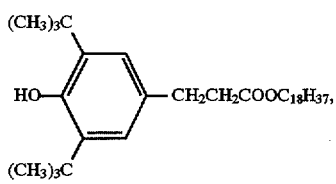

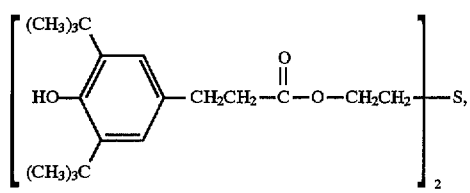

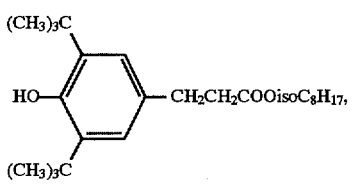

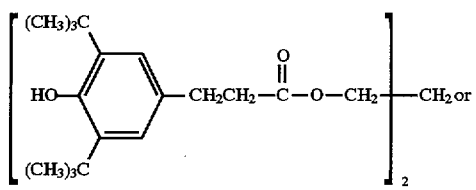

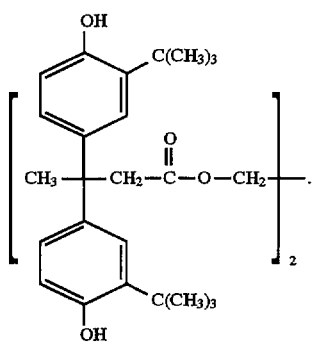

Particularly preferred compounds of the formula III are methyl 3-(3',5'-di-tert-butyl-4'-hydroxyphenyl)propionate and methyl 3-(3'-tert-butyl-4'-hydroxy-5'-methylphenyl)propionate.

In a specifically preferred manner, the invention relates to products which can be obtained by reacting components a), b) and c), the component a) being a compound of the formula, I, in particular pentaerythritol, thiodiethylene glycol, 1,4-butanediol, 1,2-propanediol, diethylene glycol, triethylene glycol, diethanolamine, glycerol,

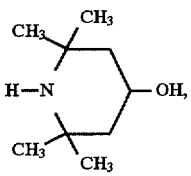

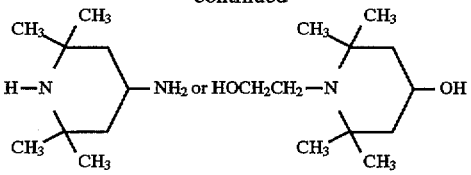

or a mixture of these, component b) is a compound of the formula H, in particular sunflower oil, coconut oil, rapeseed oil, maize germ oil, safflower oil, olive oil, groundnut oil or Radiamuls or a mixture of these, and component c) is a compound of the formula III, in particular methyl 3-(3',5'-ditertbutyl-4'-hydroxyphenyl)propionate or methyl 3-(3'-tert-butyl-4'-hydroxy-5'-methylphenyl)propionate.

The present invention furthermore relates to products which can be obtained by reacting components a), b) and c) in a molar quantitative ratio of 0.1:1:0.1 to 15:1:30. A molar quantitative ratio of 1:1:1 to 10:1:20 is preferred. A molar quantitative ratio of 4:1:5 to 10:1:20 is particularly preferred. A molar quantitative ratio of 5:1:10 is especially preferred.

The products according to the invention can comprise, for example, 30 to 80% by weight, preferably 35 to 80% by weight, in particular 50 to 80% by weight, of the active group E-2

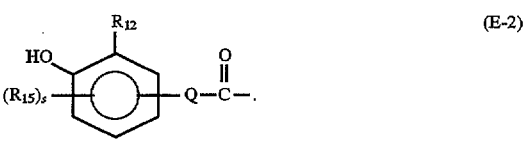

(E-2)

As already mentioned, the present products are suitable for stabilising organic materials against oxidative, thermal or light-induced degradation. Particular mention is made of their outstanding action as antioxidants in the stabilisation of organic materials.

Exemplary of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, mines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkcyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1 ), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or/and terephthalic acid and with or without an elastomer as a modifier, for example poly-2,4,4,-trimethylhexamethylene teraphthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

The invention therefore furthermore relates to compositions comprising an organic material which is sensitive to oxidative, thermal or light-induced degradation and at least one product obtainable by reacting components a), b) and c), and to the use of these products for stabilising organic material against oxidative, thermal or light-induced degradation.

The invention therefore also relates to a process for stabilising organic material against thermal, oxidative or light-induced degradation, which comprises adding, to this material, at least one product obtainable by reacting components a), b) and c).

The use of these products as antioxidants in organic materials is of particular interest.

Preferred organic materials are polymers, for example synthetic polymers, in particular thermoplastic polymers.

Particularly preferred organic materials are polyolefines and styrene copolymers, for example those mentioned above under items 1 to 3 and items 6 and 7, in particular polyethylene and polypropylene as well as ABS and styrene/butadiene copolymers. The invention therefore preferably relates to compositions in which the organic material is a synthetic organic polymer or a mixture of such polymers, in particular a polyolefin or a styrene copolymer.

As a rule, the products are added to the material to be stabilised in amounts from 0.01 to 10%, preferably 0.01 to 5%, in particular 0.01 to 2%, relative to the total weight of the material to be stabilised. It is particularly preferred to employ the products according to the invention in amounts of 0.01 to 0.5%, in particular 0.05 to 0.3%.

In addition to the product, the compositions according to the invention can also contain conventional additives, for example those mentioned below.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzyl-phosphonic acid.

1.11. Acylaminophenols, for example 4-hydroxylauranilide, 4-hyctroxystearanilide, octyl N-(3,5-di-tert-butyl-4-hydroxyphenyl)carbamate.

1.12. Esters of β-(3,5-di-tert-butyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$, where R=3'-tert-butyl-4'-hydroxy-5'-2H-benzotriazol-2-ylphenyl, 2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-terthutylphenyl salicylate, phenyl salicylate, octylphenyl salicylate, dibenzoyl resorcinol, bis (4-tert-butylbenzoyl)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butyl-amino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diidsodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazol, zinc didutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863 or U.S. Pat. No. 4,338,244.

The conventional additives are added for example at concentrations of 0.01 to 10% based on the total weight of the material to be stabilised.

The products and, if desired, other additives, can be incorporated into the organic material by known methods. They can be incorporated in the materials for example by admixing or applying the products and, if desired, other additives by the methods conventionally used in the art. If the materials are polymers, in particular synthetic polymers, the products can be incorporated before or during shaping or by applying the dissolved or dispersed products to the polymer, with or without subsequent evaporation of the solvent. In the case of elastomers, the latter can also be stabilised in the form of the latices. A further possibility of incorporating the products according to the invention into polymers is the addition of the former before, during or immediately after polymerisation of the monomers in question, or before crosslinking. The products according to the invention can be added as they are, but also in encapsulated form (for example in waxes, oils or polymers). If they are added before or during polymerisation, the products according to the invention can also act as chain length regulators for the polymers (chain terminators). The products according to the invention can also be added to the materials to be stabilised in the form of a masterbatch comprising, for example, a concentration of 2.5 to 25% by weight of the product according to the invention.

The materials which have been stabilised in this manner can be used in a multitude of ways, for example in the form of films, fibres, tapes, moulding materials, sections or as binders for varnishes, adhesives or cements.

The invention furthermore relates to compositions comprising a functional fluid, preferably from the series of the lubricants, the hydraulic fluids and the metal-working fluids as well as fuels for driving engines of the 4-stroke Otto, 2-stroke, diesel, Wankel as well as the orbital type, and at least one product obtainable by reacting components a), b) and c).

Particularly preferred as lubricants are the mineral oils, the synthetic oils or mixtures of these.

The products known per se are used as functional fluids from the series of the lubricants, the hydraulic fluids and the metal-working fluids.

The lubricants and hydraulic fluids which are suitable are known to those skilled in the art and described, for example, in Dieter Klamann "Schmierstoffe und verwandte Produkte" [Lubricants and Related Products], Verlag Chemie, Weinheim, 1982, in Schewe-Kobek, "Das Schmiermittel-Taschenbuch" [Lubricants Guide], Dr. Alfred Hüthig-Verlag, Heidelberg, 1974, or in "Ullmanns Encyclopädie der technischen Chemie" [Ullmann's Encyclopedia of Industrial Chemistry], Volume 13, pages 85–94 (Verlag Chemie, Weinheim, 1977).

Examples are lubricants and hydraulic fluids based on mineral oil or synthetic lubricants or hydraulic fluids, in particular those which are derivatives of carboxylic esters and which are used at temperatures of 200° C and above.

Examples of synthetic lubricants embrace lubricants based on a diester of a dibasic acid with a monovalent alcohol, for example dioctyl sebacate or dinonyl adipate, a triester of trimethylolpropane with a monobasic acid or a mixture of such acids, for example trimethylolpropane tripelargonate, trimethylolpropane tricaprylate or mixtures of these, a tetraester of pentaerythritol with a monobasic acid or with a mixture of such acids, for example pentaerythritol tetracaprylate, or a complex ester of monobasic and dibasic acids with polyhydric alcohols, for example a complex ester of trimethylolpropane with caprylic and sebacic acid or a mixture of these.

Particularly suitable are, besides mineral oils, for example poly-α-olefins, lubricants based on esters, or phosphates, glycols, polyglycols and polyalkylene glycols, and mixtures of these with water.

The products according to the invention are oils and readily soluble in lubricants and therefore particularly suitable as additives to lubricants, and mention must be made of their surprisingly good antioxidative and anticorrosive action.

The products according to the invention can display their surprising properties for example in lubricants for combustion engines, for example in combustion engines operating by the Otto principle. The products according to the invention prevent the formation of deposits (sludge), or reduce these deposits to a surprising extent.

So-called masterbatches can also be prepared.

The products according to the invention are active as additives in lubricants even when used in very small amounts. They are admixed to the lubricants advantageously in an amount of 0.01 to 5% by weight, preferably in an amount of 0.05 to 3% by weight and particularly preferably in an amount of 0.1 to 2% by weight, in each case based on the lubricant.

The lubricants can additionally comprise other additives which are added to improve the basic properties of lubricants even further; these include: antioxidants, metal passivators, rust inhibitors, viscosity index improvers, pour-point depressers, dispersants, detergents, high-pressure additives, antifriction additives and antiwear additives.

A series of such compounds can be found, for example, in the above list "1. Antioxidants", in particular items 1.1 to 1.16. The following additives must be mentioned additionally by way of example:

Examples of aminic antioxidants:

N,N'-diisopropyl-p-phenylenediamine, N,N'-di-sec-butyl-p-phenylenediamine, N,N'-bis-(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis-(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one and 2,2,6,6-tetramethylpiperidin-4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14- tetrathiahexadecane.

Examples of metal deactivators, for example for copper, are:
a) Benzotriazoles and derivatives thereof, for example 4- or 5-alkylbenzotriazoles (e.g. tolutriazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl)tolutriazole and 1-[bis(2-ethylhexyl)aminomethyl)benzotriazole; and alkoxyalkylbenzotriazoles such as 1-(nonyloxyraethyl)benzotriazole, 1-(1-butoxyethyl)benzotriazole and 1-(1-cyclohexyloxybutyl)tolutriazole.
b) 1,2,4-Triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.
c) Imidazole derivatives, for example 4,4'-methylenebis(2-undecyl-5-methylimidazole) and bis[(N-methyl)imidazol-2-yl]carbinol octyl ether.
d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one.
e) Amino compounds, for example salicylidenepropylenediamine, salicylaminoguanidine and salts thereof.

Examples of rust inhibitors are:
a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-carboxymethyl-1-dodecyl-3-methylglycerol and the amine salts thereof.
b) Nitrogen-containing compounds, for example:
   I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.
   II. Heterocyclic compounds, for example: substituted imidazolines and oxazolines, and 2-heptadecenyl-1-(2-hydroxyethyl)imidazoline.
c) Phosphorus-containing compounds, for example: Amine salts of phosphoric acid partial esters or phosphonic acid partial esters, and zinc dialkyldithiophosphates.
d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and salts thereof.
e) Glycerol derivatives, for example: glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols.

Examples of viscosity index improvers are: Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are: Polymethacrylate and alkylated naphthalene derivatives.

Examples of dispersants/surfactants are: Polybutenylsuccinic amides or -imides, polybutenylphosphonic acid derivatives and basic magnesium, calcium and barium sulfonates and phenolates.

Examples of antiwear additives are: Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl)thio]propionate, triphenyl thiophosphate (triphenylphosphorothioate), tris(alkylphenyl)phosphorothioate and mixtures thereof (for example tris (isononylphenyl)phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris [isooctyl 2-acetate], derivatives of 2-mercaptobenzothiazole such as 1-[N,N-bis-(2-ethylhexyl)aminomethyl]-2-mercapto-1H-1,3-benzothiazole, and ethoxycarbonyl-5-octyldithiocarbamate.

The examples which follow illustrate the invention in greater detail. Parts and percentages are by weight, unless otherwise indicated.

EXAMPLE 1

Preparation of the sunflower oil derivatives using pentaerythritol and methyl 3-(3',5'-di-tert-butyl-4'-hydroxyphenyl)propionate.

In a sulfonation flask equipped with reflux condenser and mechanical stirrer, a mixture of 30 g (~34 mmol) sunflower oil, 4.64 g (34 mmol) of pentaerythritol and 37 mg (0.15 mmol) of dibutyltin oxide is kept under nitrogen for 7 hours at 180°–190° C. 9.94 g (34 mmol) of methyl 3-(3',5'-di-tert-butyl-4'-hydroxyphenyl)propionate and another 37 mg (0.15 mmol) of dibutyltin oxide are subsequently added. Stirring of the reaction mixture is continued for 15 hours at 180°–190° C. When cold, 40.64 g (91%) of product are obtained as a yellow oil having a refractive index $n_D^{20}$ of 1.4882.

EXAMPLE 2

Preparation of the coconut oil derivatives using pentaerythritol and methyl 3-(3',5'-di-tert-butyl-4'-hydroxyphenyl)propionate.

The procedure described in Example 1 is repeated, except that 403 g (~0.616 mol) of coconut fat, 83.1 g (0.610 mol) of pentaerythritol, 1.0 g (4 mmol) of dibutyltin oxide and 178.4 g (0.610 mol) of methyl 3-(3',5'-di-tert-butyl-4'-hydroxyphenyl)propionate are used, affording 653 g (98%) of product as a brown oil having a refractive index $n_D^{20}$ of 1.4781.

EXAMPLE 3

Preparation of the sunflower oil derivatives using thiodiethylene glycol and methyl 3-(3',5'-di-tert-butyl-4'-hydroxyphenyl)propionate.

The procedure described in Example 1 is repeated, except that 50 g (~57 mmol) of sunflower oil, 41.8 g (343 mmol) of thiodiethylene glycol, 448 mg (1.8 mmol) of dibutyltin oxide and 200 g (684 mmol) of methyl 3-(3',5'-di-tert-butyl-4'-hydroxyphenyl)propionate are used, affording 279.1 g (96%) of product as a yellow oil with a refractive index $n_D^{20}$ of 1.5170.

EXAMPLE 4

Preparation of the coconut oil derivatives using thiodiethylene glycol and methyl 3-(3',5'-di-tert-butyl-4'-hydroxyphenyl)propionate.

The procedure described in Example 1 is repeated, except that 49.9 g (~76 mmol) of coconut fat, 85.1 g (688 mmol) of thiodiethylene glycol, 797 mg (3.2 mmol) of dibutyltin oxide and 402.6 g (1.38 mol) of methyl 3-(3',5'-di-tert-butyl-4'-hydroxyphenyl)propionate are used, affording 500.7 g (93%) of product as a brownish orange oil having a refractive index $n_D^{20}$ of 1.5210.

EXAMPLE 5

Preparation of the sunflower oil derivatives using 1,4-butanediol and methyl 3-(3',5'-di-tert-butyl-4'-hydroxyphenyl)propionate. The procedure described in Example 1 is repeated, except that 30 g (~34 mmol) sunflower oil, 14 g (155 mmol) of 1,4-butanediol, 199 mg (0.80 mmol) of dibutyltin oxide and 87.7 g (300 mmol) of methyl 3-(3',5'-di-tert-butyl-4'-hydroxyphenyl)propionate are used, affording 124 g (94%) of product as a reddish oil having a refractive index $n_D^{20}$ of 1.5070.

EXAMPLE 6

Preparation of the coconut oil derivatives using 1,4-butanediol and methyl 3-(3',5'-di-tert-butyl-4'-hydroxyphenyl)propionate.

The procedure described in Example 1 is repeated, except that 30 g (~46 mmol) of coconut fat, 14 g (155 mmol) of 1,4-butanediol, 199 mg (0.80 mmol) of dibutyltin oxide and 87.7 g (300 mmol) of methyl 3-(3',5'-di-tert-butyl-4'-hydroxyphenyl)propionate are used, affording 123 g (93%) of product as a reddish oil with a refractive index $n_D^{20}$ of 1.5025.

EXAMPLE 7

Preparation of the sunflower oil derivatives using 1,2-propanediol and methyl 3-(3',5'-di-tert-butyl-4'-hydroxyphenyl)propionate.

The procedure described in Example 1 is repeated, except that 30 g (~34 mmol) of sunflower oil, 12.2 g (160 mmol) of 1,2-propanediol, 199 mg (0.80 mmol) of dibutyltin oxide and 87.7 g (300 mmol) of methyl 3-(3',5'-di-tert-butyl-4'-hydroxyphenyl)propionate are used, affording 121.7 g (93.7%) of product as a yellow oil having a refractive index $n_D^{20}$ of 1.5047.

EXAMPLE 8

Preparation of the sunflower oil derivatives using diethylene glycol and methyl 3-(3',5'-di-tert-butyl-4'-hydroxyphenyl)propionate.

The procedure described in Example 1 is repeated, except that 30.1 g (~34 mmol) of sunflower oil, 16.7 g (157 mmol) of diethylene glycol, 199 mg (0.80 mmol) of dibutyltin oxide and 89.5 g (306 mmol) of methyl 3-(3',5'-di-tert-butyl-4'-hydroxyphenyl)propionate are used, affording 137.3 g (99%) of product as a yellow oil having a refractive index $n_D^{20}$ of 1.5065.

EXAMPLE 9

Preparation of the coconut oil derivatives using diethylene glycol and methyl 3-(3',5'-di-tert-butyl-4'-hydroxyphenyl)propionate.

The procedure described in Example 1 is repeated, except that 30 g (~46 mmol) of coconut fat, 22.3 g (210 mmol) of diethylene glycol, 249 mg (1.00 mmol) of dibutyltin oxide and 121.1 g (414 mmol) of methyl 3-(3',5'-di-tert-butyl-4'-hydroxyphenyl)propionate are used, affording 158.1 g (91%) of product as a yellow oil with a refractive index $n_D^{20}$ of 1.5068.

EXAMPLE 10

Preparation of the sunflower oil derivatives using triethylene glycol and methyl 3-(3',5'-di-tert-butyl-4'-hydroxyphenyl)propionate.

The procedure described in Example 1 is repeated, except that 30 g (~34 mmol) of sunflower oil, 15 g (100 mmol) of triethylene glycol, 199 mg (0.80 mmol) of dibutyltin oxide and 90.65 g (310 mmol)of methyl 3-(3',5'-di-tert-butyl-4'-hydroxyphenyl)propionate are used, affording 129 g (95%) of product as a pale yellow oil having a refractive index $n_D^{20}$ of 1.5050.

EXAMPLE 11

Preparation of the coconut oil derivatives using triethylene glycol and methyl 3-(3',5'-di-tert-butyl-4'-hydroxyphenyl)propionate.

The procedure described in Example 1 is repeated, except that 30 g (~46 mmol) of coconut fat, 15.2 g (100 mmol) of triethylene glycol, 199 mg (0.80 mmol) of dibutyltin oxide and 90.65 g (310 mmol) of methyl 3-(3',5'-di-tert-butyl-4'-hydroxyphenyl)propionate are used, affording 129.5 g (95%) of product as a pale yellow oil having a refractive index $n_D^{20}$ of 1.4992.

EXAMPLE 12

Preparation of the Radiamuls derivatives using diethylene glycol and methyl 3-(3',5'-di-tert-butyl-4'-hydroxyphenyl)propionate.

The procedure described in Example 1 is repeated, except that 30 g (~59 mmol) of Radiamuls (glycerol tri $C_8/C_{10}$), 16.3 g (154 mmol) of diethylene glycol, 224 mg (0.90 mmol) of dibutyltin oxide and 95.6 g (327 mmol) of methyl 3-(3',5'-di-tert-butyl-4'-hydroxyphenyl)propionate are used, affording 132.6 g (99%) of product as a pale yellow oil having a refractive index $n_D^{20}$ of 1.5022.

EXAMPLE 13

Preparation of the sunflower oil derivatives using diethanolamine and methyl 3-(3',5'-di-tert-butyl-4'-hydroxyphenyl)propionate.

The procedure described in Example 1 is repeated, except that 60 g (~68 mmol) of sunflower oil, 14.3 g (136 mmol) of diethanolamine, 149 mg (0.60 mmol) of dibutyltin oxide and 19.9 g (68 mmol) of methyl 3-(3',5'-di-tert-butyl-4'-hydroxyphenyl)propionate are used, affording 88.4 g (95%) of product as a brownish red oil having a refractive index $n_D^{20}$ of 1.4940.

EXAMPLE 14

Preparation of the coconut oil derivatives using diethanolamine and methyl 3-(3',5'-di-tert-butyl-4'-hydroxyphenyl)propionate.

The procedure described in Example 1 is repeated, except that 60 g (~92 mmol) of coconut fat, 19.1 g (182 mmol) of diethanolamine, 174 mg (0.70 mmol) of dibutyltin oxide and 34.2 g (117 mmol) of methyl 3-(3',5'-di-tert-butyl-4'-hydroxyphenyl)propionate are used, affording 104.9 g (93%) of product as a brown oil having a refractive index $n_D^{20}$ of 1.4905.

EXAMPLE 15

Preparation of the sunflower oil derivatives using glycerol and methyl 3-(3',5'-di-tert-butyl-4'-hydroxyphenyl) propionate.

The procedure described in Example 1 is repeated, except that 30 g (~34 mmol) of sunflower oil, 14.22 g (154 mmol) of glycerol, 199 mg (0.80 mmol) of dibutyltin oxide and 87.73 g (300 mmol) of methyl 3-(3',5'-di-tert-butyl-4'-hydroxyphenyl)propionate are used, affording 126.5 g (96%) of product as a pale yellow, viscous oil having a refractive index $n_D^{20}$ of 1.5128.

EXAMPLE 16

Preparation of the coconut oil derivatives using glycerol and methyl 3-(3',5'-di-tert-butyl-4'-hydroxyphenyl)propionate.

The procedure described in Example 1 is repeated, except that 30 g (~46 mmol) of coconut fat, 19.4 g (211 mmol) of glycerol, 249 mg (1.0 mmol) of dibutyltin oxide and 118 g (404 mmol) of methyl 3-(3',5'-di-tert-butyl-4'-hydroxyphenyl)propionate are used, affording 154 g (92%) of product as a pale yellow, viscous oil having a refractive index $n_D^{20}$ of 1.5123.

EXAMPLE 17

Preparation of the sunflower oil derivatives using glycerol and methyl 3-(3'-tert-butyl-4'-hydroxy-5'-methylphenyl) propionate.

The procedure described in Example 1 is repeated, except that 30 g (~34 mmol) of sunflower oil, 14.5 g (157 mmol) of glycerol, 180 mg (0.72 mmol) of dibutyltin oxide and 75.20 g (300 mmol) of methyl 3-(3'-tert-butyl-4'-hydroxy-5'-methylphenyl)propionate are used, affording 105.0 g (96%) of product as an orange oil having a refractive index $n_D^{20}$ of 1.5165.

EXAMPLE 18

Preparation of the coconut oil derivatives using diethylene glycol and methyl 3-(3'-tert-butyl-4'-hydroxy-5'-methylphenyl)propionate.

The procedure described in Example 1 is repeated, except that 30 g (~46 mmol) of coconut fat, 22.6 g (213 mmol) of diethylene glycol, 184 mg (0.70 mmol) of dibutyltin oxide and 94.3 g (390 mmol) of methyl 3-(3'-tert-butyl-4'-hydroxy-5'-methylphenyl)propionate are used, affording 131.9 g (98%) of product as a yellow oil having a refractive index $n_D^{20}$ of 1.5118.

EXAMPLE 19

Preparation of the sunflower oil derivatives using 4-hydroxy-2,2,6,6-tetramethylpiperidine and methyl 3-(3',5'-di-tert-butyl-4'-hydroxyphenyl)propionate.

The procedure described in Example 1 is repeated, except that 41.5 g (~47 mmol) of sunflower flower oil, 7.90 g (50 mmol) of 4-hydroxy-2,2,6,6-tetramethylpiperidine, 50 mg (0.20 mmol) of dibutyltin oxide and 14.60 g (50 mmol) of methyl 3-(3',5'-di-tert-butyl-4'-hydroxyphenyl)propionate are used, affording 59.4 g (95%) of product as a brown oil having a refractive index $n_D^{20}$ of 1.4848.

EXAMPLE 20

Preparation of the sunflower oil derivatives using 4-amino-2,2,6,6-tetramethylpiperidine and methyl 3-(3',5'-di-tert-butyl-4'-hydroxyphenyl)propionate.

The procedure described in Example 1 is repeated, except that 41.5 g (~47 mmol) of sunflower oil, 7.80 g (50 mmol) of 4-amino-2,2,6,6-tetramethylpiperidine, 50 mg (0.20 mmol) of dibutyltin oxide and 14.60 g (50 mmol) of methyl 3-(3',5'-di-tert-butyl-4'-hydroxyphenyl)propionate are used, affording 61.8 g (99%) of product as a brown oil having a refractive index $n_D^{20}$ of 1.4887.

EXAMPLE 21

Preparation of the coconut oil derivatives using N-(2-hydroxyethyl)-4-hydroxy-2,2,6,6-tetramethylpiperidine and methyl 3-(3',5'-di-tert-butyl-4'-hydroxyphenyl)propionate.

The procedure described in Example 1 is repeated, except that 31.0 g (~47 mmol) of coconut nut fat, 10.1 g (50 mmol)of N-(2-hydroxyethyl)-4-hydroxy-2,2,6,6-tetramethylpiperidine, 50 mg (0.20 mmol) of dibutyltin oxide and 14.60 g (50 mmol) of methyl 3-(3',5'-di-tert-butyl-4'-hydroxyphenyl)propionate are used, affording 52.4 g (98%) of product as a yellow oil having a refractive index $n_D^{20}$ of 1.4811.

EXAMPLE 22

Preparation of the rapeseed oil derivatives using glycerol and methyl 3-(3',5'-di-tert-butyl-4'-hydroxyphenyl) propionate.

In a sulfonation flask equipped with reflux condenser and mechanical stirrer, a mixture of 116.3 g (~134 mmol) of rapeseed oil, 86.1 g (935 mmol) of 85% aqueous glycerol and 2.64 g (15.0 mmol) of calcium acetate is kept for 7 hours under a nitrogen atmosphere at 180°–190° C. 357.5 g (1.22 mol) of methyl 3-(3',5'-di-tert-butyl-4'-hydroxyphenyl) propionate are subsequently added. Stirring of the reaction mixture is continued for 15 hours at 180°–190° C. After cooling, 505 g (99%) of product are obtained as a yellow oil having a refractive index $n_D^{20}$ of 1.5122.

EXAMPLE 23

Preparation of the maize germ oil derivatives using glycerol and methyl 3-(3',5'-di-tert-butyl-4'-hydroxyphenyl) propionate.

The procedure described in Example 22 is repeated, except that 100 g (~113 mmol) of maize germ oil, 57.5 g (624 mmol) of 85% aqueous glycerol, 2.32 g (13.0 mmol) of calcium acetate and 282.4 g (966 mmol) of methyl 3-(3',5'-di-tert-butyl-4'-hydroxyphenyl)propionate are used, affording 399.0 g (99%) of product as a yellow oil having a refractive index $n_D^{20}$ of 1.5127.

EXAMPLE 24

Preparation of the safflower oil derivatives using glycerol and methyl 3-(3',5'-di-tert-butyl-4'-hydroxyphenyl) propionate.

The procedure described in Example 22 is repeated, except that 100 g (~113 mmol) of safflower oil, 57.6 g (625 mmol) of 85% aqueous glycerol, 2.11 g (12.0 mmol) of calcium acetate and 286.5 g (980 mmol) of methyl 3-(3',5'-di-tert-butyl-4'-hydroxyphenyl)propionate are used, affording 403.2 g (99%) of product as a yellow oil having a refractive index $n_D^{20}$ of 1.5140.

EXAMPLE 25

Preparation of the olive oil derivatives using glycerol and methyl 3-(3',5'-di-tert-butyl-4'-hydroxyphenyl)propionate.

The procedure described in Example 22 is repeated, except that 100 g (~114 mmol) of olive oil, 58.0 g (630 mmol) of 85% aqueous glycerol, 2.11 g (12.0 mmol) of calcium acetate and 290.4 g (993 mmol) of methyl 3-(3',5'-di-tert-butyl-4'-hydroxyphenyl)propionate are used, affording 408.6 g (99%) of product as a yellow oil having a refractive index $n_D^{20}$ of 1.5110.

EXAMPLE 26

Preparation of the groundnut oil derivatives using glycerol and methyl 3-(3',5'-di-tert-butyl-4'-hydroxyphenyl) propionate.

The procedure described in Example 22 is repeated, except that 100 g (~114 mmol) of groundnut oil, 58.0 g (630 mmol) of 85% aqueous glycerol, 2.11 g (12.0 mmol) of calcium acetate and 291.4 g (997 mmol) of methyl 3-(3',5'-di-tert-butyl-4'-hydroxyphenyl)propionate are used, affording 413.5 g (99%) of product as a yellow oil having a refractive index $n_D^{20}$ of 1.5100.

EXAMPLE 27

Deposit and Oxidation Panel Test (DOPT)

The deposit and oxidation panel test (DOPT) is a variant of a test method for engine oils, in particular diesel engine oils, which has been described by G. Abellaneda et at. IIIè Symposium CEC, 1989, 61, New Cavendish Street, London W1M 8AR, England. The suitability of the oils with stabiliser for preventing deposits on the pistons is tested.

The test time is 20 hours, the panel temperature 260° C. and the oil flex 1 ml/minutes. The humid atmospheric environment is enriched with 260 ppm of $NO_2$ and 26 ppm of $SO_2$. After the test, the metal panel onto which the oil drops, is weighed and assessed visually. The lower the numbers, the better. The lubricating oil used is a commercial CD oil which is diluted with the basic oil STANCO 150. The stabilisers shown in Table 1 are now admixed to this prepared oil in amounts of 0.6% by weight based on the oil, and this is subjected to a DOPT test.

TABLE 1

"Deposit and Oxidation Panel Test" (DOPT)

| Product according to | Concentration | Deposits on panel | |
|---|---|---|---|
| Example | in % by weight | Weight (mg) | Visual assessment |
| 8 | 0.6 | 14 | 4 |
| 9 | 0.6 | 10 | 4 |
| 10 | 0.6 | 11 | 6 |
| 15 | 0.6 | 14 | 6 |
| no additive | no additive | 72 | 14 |

What is claimed is:

1. A composition comprising

α) an organic material subject to oxidative, thermal or light-induced degradation, and β) an effective stabilizing amount of at least one product obtainable by reacting components a), b) and c) in a molar ratio of a), b) and c) which is 0.1:1:0.1 to 15:1:30, wherein component a) is a compound of formula I or a mixture of compounds of formula I, component b) is a compound of formula II or a mixture of compounds of formula II, and component c) is a compound of formula III or a mixture of compounds of formula III,

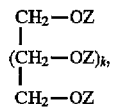

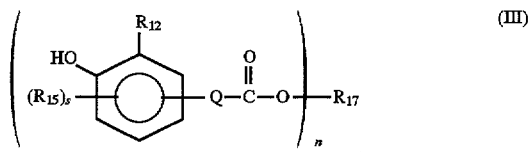

in which, in the compound of formula I,
the radicals Y are OH,
a is the number 1, 2, 3, 4 or 6, where,
when Y is OH and a is 1,
X is $C_1-C_{45}$alkyl, $C_3-C_{18}$alkenyl or $-CH_2CH_2T_1(CH_2CH_2O)_bR_4$,
$T_1$ is oxygen or sulfur,
$R_4$ is $C_1-C_{20}$alkyl,
b is an integer ranging from 0 to 10,
when Y is OH and a is 2,
X is $-CH_2CH_2T_2(CH_2CH_2O)_bCH_2CH_2-$, in which b is as defined above, $-C_cH_{2c}-$, $-CH_2-CH=CH-CH_2-$ or

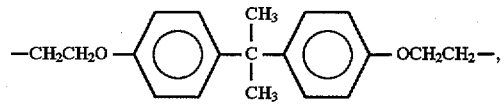

in which
$T_2$ is oxygen, sulfur or

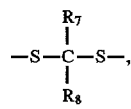

c is an integer ranging from 2 to 10,
$R_7$ and $R_8$ independently of one another are hydrogen, $C_1-C_{18}$alkyl or phenyl, or $R_7$ and $R_8$ together with the C atom to which they are bonded form a $C_5-C_{12}$cycloalkyl ring, or
when a is 3,
X is $C_3-C_{10}$alkanetriyl or,
when Y is OH and a is 4,
X is $C_4-C_{10}$alkanetetrayl,

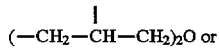

or

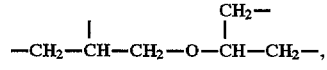

or
when Y is OH and a is 6,
X is

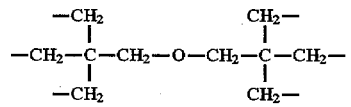

or $C_6-C_{10}$alkanehexayl;

in the compound of the formula II, the radicals Z are hydrogen or a group of the formula

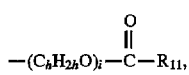

k is an integer ranging from 0 to 6, in which
h is 2 or 3,
i is an integer ranging from 0 to 12, and
$R_{11}$ is $C_1-C_{30}$alkyl, $C_8-C_{30}$alkenyl, $C_5-C_{12}$cycloalkyl, phenyl or $C_7-C_9$phenylalkyl, with the proviso that the compound of the formula II has a group

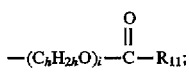

and
in the compound of the formula III,
$R_{12}$ is $C_1-C_{18}$alkyl, $C_5-C_{12}$cycloalkyl, phenyl or $C_7-C_9$phenylalkyl,
$R_{15}$ is hydrogen, $C_1-C_{18}$alkyl, $C_5-C_{12}$cycloalkyl, phenyl or $C_7-C_9$phenylalkyl,
s is 0, 1 or 2,
Q is

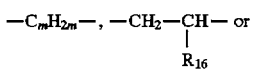

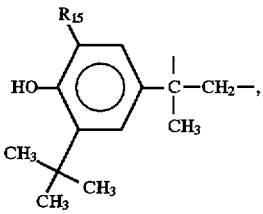

in which $R_{15}$ is as defined above,
m is an integer ranging from 0 to 3,
$R_{16}$ is $C_1-C_8$alkyl, and
n is an integer ranging from 1 to 6, where,
when n is 1,
$R_{17}$ is hydrogen, $C_1-C_{45}$alkyl, $C_5-C_{12}$cycloalkyl, $C_2-C_{18}$alkenyl, a monovalent radical of a hexose, a monovalent radical of a hexitol,

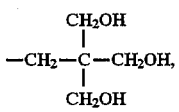

or furthermore $R_{17}$ is —$CH_2CH_2$—$T_3$—$R_{19}$ or

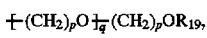

in which
$T_3$ is oxygen or sulfur, $R_{19}$ is

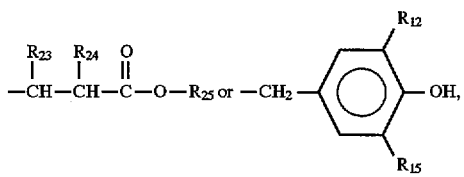

in which $R_{12}$ and $R_{15}$ are as defined above, or $R_{19}$ is furthermore hydrogen, $C_1-C_{24}$alkyl, phenyl, $C_5-C_{12}$cycloalkyl or

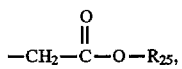

in which
p is an integer ranging from 2 to 4,
q is an integer ranging from 2 to 20,
$R_{23}$ and $R_{24}$ independently of one another are hydrogen or methyl, with the proviso that $R_{23}$ and $R_{24}$ are not simultaneously methyl;
$R_{25}$ is hydrogen or $C_1-C_{24}$alkyl, or,
when n is 2,
$R_{17}$ is a divalent radical of a hexose, a divalent radical of a hexitol,

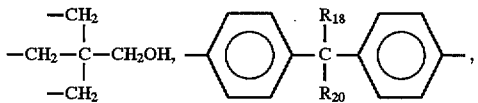

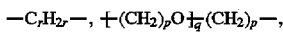

in which p and q are as defined above,
—$CH_2CH_2$—$T_4$—$CH_2CH_2$—, —$CH_2$—$CH$=$CH$—$CH_2$— or —$CH_2$—$C$≡$C$—$CH_2$—, in which $R_{18}$ and $R_{20}$ independently of one another are hydrogen or $C_1-C_{12}$alkyl or together are the radical —$CH_2CH_2CH_2CH_2CH_2$—,
r is an integer ranging from 2 to 10,
$T_4$ is sulfur or

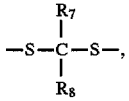

in which $R_7$ and $R_8$ are as defined above, or
when n is 3
$R_{17}$ is a trivalent radical of a hexose, a trivalent radical of a hexitol or

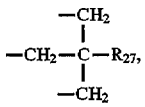

in which
$R_{27}$ is hydrogen, $CH_2OH$ or $C_1-C_4$alkyl, or
when n is 4,
$R_{17}$ is a tetravalent radical of a hexose, a tetravalent radical of a hexitol or $C_4-C_{10}$alkanetetrayl, or when n is 5,
  $R_{17}$ is a pentavalent radical of a hexose or a pentavalent radical of a hexitol, or,
when n is 6,
  $R_{17}$ is a hexavalent radical of a hexitol or $$-CH_2-\underset{\underset{-CH_2}{|}}{\overset{\overset{-CH_2}{|}}{C}}-CH_2-O-CH_2-\underset{\underset{CH_2-}{|}}{\overset{\overset{CH_2-}{|}}{C}}-CH_2-.$$

2. A composition as claimed in claim 1 in which in component β), in the compound of formula III, s is the number 1 or 2.

3. A composition as claimed in claim 1 in which in component β), in the compound of formula I, the radicals Y are OH, and
a is the number 1, 2, 3, 4 or 6, where,
when Y is OH and a is 1,
  X is $C_1$–$C_{30}$alkyl, $C_3$–$C_{18}$alkenyl or —$CH_2CH_2T_1(CH_2CH_2O)_bR_4$,
  $T_1$ is oxygen or sulfur,
  $R_4$ is $C_1$–$C_{10}$alkyl,
  b is an integer ranging from 0 to 10, or
when Y is OH and a is 2,
  X is —$CH_2CH_2T_2(CH_2CH_2O)_bCH_2CH_2$—, in which b is as defined above, $$-C_cH_{2c}-,\ -CH_2-CH=CH-CH_2-\ \text{or}$$

$$-CH_2CH_2O-\!\!\bigcirc\!\!-\underset{\underset{CH_3}{|}}{\overset{\overset{CH_3}{|}}{C}}-\!\!\bigcirc\!\!-OCH_2CH_2-,$$

in which
$T_2$ is oxygen, sulfur or $$-S-\underset{\underset{R_8}{|}}{\overset{\overset{R_7}{|}}{C}}-S-,$$

and
c is an integer ranging from 2 to 10,
$R_7$ and $R_8$ independently of one another are hydrogen, $C_1$–$C_{10}$alkyl or phenyl, or $R_7$ and $R_8$ together with the C atom to which they are bonded form a $C_5$–$C_7$cycloalkyl ring;
in the compound of the formula II,
the radicals Z are hydrogen or a group of the formula $$-(C_hH_{2h}O)_i-\overset{\overset{O}{\|}}{C}-R_{11}$$

and
k is an integer ranging from 0 to 4, in which
h is 2 or 3,
i is an integer ranging from 0 to 6 and
$R_{11}$ is $C_1$–$C_{20}$alkyl, $C_8$–$C_{20}$alkenyl, $C_5$–$C_7$cycloalkyl, phenyl or benzyl, with the proviso that the compound of the formula II comprises a group $$-(C_hH_{2h}O)_i-\overset{\overset{O}{\|}}{C}-R_{11};$$

and
in the compound of the formula III
$R_{12}$ is $C_1$–$C_6$alkyl, $C_5$–$C_7$cycloalkyl, phenyl or benzyl
$R_{15}$ is hydrogen, $C_1$–$C_6$alkyl, $C_5$–$C_7$cycloalkyl, phenyl or benzyl,
s is 1 or 2,
Q is $$-C_mH_{2m}-,\ -CH_2-\underset{\underset{R_{16}}{|}}{CH}-\ \text{or}$$

$$HO-\!\!\bigcirc\!\!\overset{R_{15}}{\underset{\underset{CH_3}{\overset{CH_3}{|}}C\underset{CH_3}{|}}{|}}-\underset{\underset{CH_3}{|}}{\overset{\overset{|}{|}}{C}}-CH_2-,$$

in which $R_{15}$ is as defined, above,
m is an integer ranging from 0 to 3,
$R_{16}$ is $C_1$–$C_4$alkyl and
n is an integer ranging from 1 to 6, where,
when n is 1,
  $R_{17}$ is hydrogen, $C_1$–$C_{30}$alkyl, $C_5$–$C_7$cycloalkyl, $C_2$–$C_{18}$alkenyl, a monovalent radical of a hexose, a monovalent radical of a hexitol or $$-CH_2-\underset{\underset{CH_2OH}{|}}{\overset{\overset{CH_2OH}{|}}{C}}-CH_2OH,$$

or furthermore $R_{17}$ is —$CH_2CH_2$—$T_3$—$R_{19}$ or $$+(CH_2)_pO\}_q(CH_2)_pOR_{19},$$

in which
$T_3$ is oxygen or sulfur,
$R_{19}$ is $$-\underset{\underset{}{}}{\overset{\overset{R_{23}}{|}}{CH}}-\underset{\underset{}{}}{\overset{\overset{R_{24}}{|}}{CH}}-\overset{\overset{O}{\|}}{C}-O-R_{25},\ -CH_2-\!\!\bigcirc\!\!\overset{R_{12}}{\underset{R_{15}}{-OH,}}$$

in which $R_{12}$ and $R_{15}$ are as defined above, or $R_{19}$ is furthermore hydrogen, $C_1$–$C_{18}$alkyl, phenyl, $C_5$–$C_7$cycloalkyl or $$-CH_2-\overset{\overset{O}{\|}}{C}-O-R_{25},$$

in which p is an integer ranging from 2 to 4,
q is an integer ranging from 2 to 20, $R_{23}$ and $R_{24}$ independently of one another are hydrogen or methyl with the proviso that $R_{23}$ and $R_{24}$ are not simultaneously methyl;

$R_{25}$ is hydrogen or $C_1$–$C_{18}$alkyl, or, when n is 2, $R_{17}$ is a divalent radical of a hexose, a divalent radical of a hexitol,

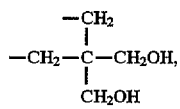

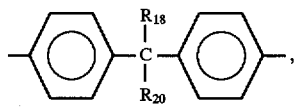

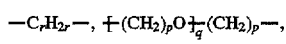

in which p and q are as defined above, —$CH_2CH_2$—$T_4$—$CH_2CH_2$—, —$CH_2$—$CH$=$CH$—$CH_2$— or —$CH_2$—$C$≡$C$—$CH_2$—, in which $R_{18}$ and $R_{20}$ independently of one another are hydrogen or $C_1$–$C_6$alkyl or together are the radical —$CH_2CH_2CH_2CH_2CH_2$—, r is an integer ranging from 2 to 10, and $T_4$ is sulfur or

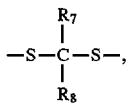

in which $R_7$ and $R_8$ are as defined above.

4. A composition as claimed in claim 1, in which in component β), in the compound of the formula I, the radicals Y are OH, $R_1$ is hydrogen or $C_1$–$C_4$alkyl, a is the number 1, 2, 3, 4 or 6, where, when Y is OH and a is 1, X is $C_1$–$C_{18}$alkyl, $C_3$–$C_{18}$alkenyl or —$CH_2CH_2T_1$($CH_2CH_2O)_bR_4$, $T_1$ is oxygen, $R_4$ is $C_1$–$C_4$alkyl, and b is an integer ranging from 0 to 10, or, when Y is OH and a is 2, X is —$CH_2CH_2T_2(CH_2CH_2)_bCH_2CH_2$—, in which b is as defined above, or furthermore X is —$C_cH_{2c}$— or —$CH_2$—$CH$=$CH$—$CH_2$—, in which $T_2$ is oxygen or sulfur, b is the number 0 or 1 and c is an integer ranging from 2 to 8, or, when a is 3, X is

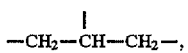

or, when Y is OH and a is 4,

X is

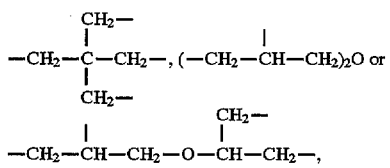

or, when Y is OH and a is 6,

X is

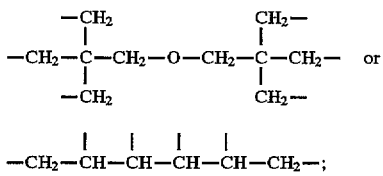

in the compound of the formula II, the radicals Z are hydrogen or a group of the formula

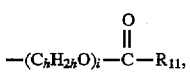

k is 1, 2 or 3, h is 2 or 3, i is an integer ranging from 0 to 4, and $R_{11}$ is $C_1$–$C_{20}$alkyl or $C_8$–$C_{20}$alkenyl, with the proviso that the compound of the formula II comprises a group

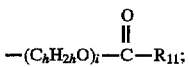

and in the compound of the formula III, $R_{12}$ is $C_1$–$C_6$alkyl or $C_5$–$C_7$cycloalkyl, $R_{15}$ is is hydrogen, $C_1$–$C_6$alkyl or $C_5$–$C_7$cycloalkyl, s is 1 or 2, Q is —$C_mH_{2m}$— or

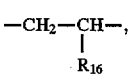

m is an integer ranging from 0 to 3, $R_{16}$ is $C_1$–$C_4$alkyl and n is an integer ranging from 1 to 6, where, when n is 1, $R_{17}$ is hydrogen, $C_1$–$C_{18}$alkyl, $C_5$–$C_7$cycloalkyl, $C_2$–$C_{18}$alkenyl, a monovalent radical of a hexose, a monovalent radical of a hexitol or

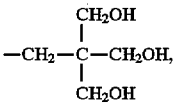

or furthermore $R_{17}$ is

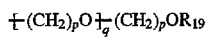

in which
$R_{19}$ is hydrogen, $C_1$–$C_{18}$alkyl or $C_5$–$C_7$cycloalkyl, in which
p is an integer ranging from 2 to 4,
q is an integer ranging from 2 to 10, or,
when n is 2,
$R_{17}$ is a divalent radical of a hexose, a divalent radical of a hexitol,

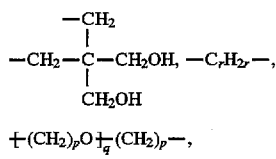

in which p and q are as defined above, or
—$CH_2CH_2$—$T_4$—$CH_2CH_2$—, in which
r is an integer ranging from 2 to 10,
$T_4$ is sulfur, or
when n is 3,
$R_{17}$ is a trivalent radical of a hexose or a trivalent radical of a hexitol, or
when n is 4,
$R_{17}$ is a tetravalent radical of a hexose, a tetravalent radical of a hexitol or

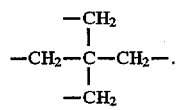

5. A composition as claimed in claim 1 in which in component β), in the compound of formula I,
the radicals Y are hydroxyl,
a is an integer ranging from 2 to 4, where,
when Y is OH and a is 2,
X is —$CH_2CH_2T_2(CH_2CH_2O)_bCH_2CH_2$— or —$C_cH_{2c}$—,
in which $T_2$ is oxygen or sulfur,
b is the number 0 or 1,
c is the number 2, 3 or 4, or,
when Y is OH and a is 3,
X is

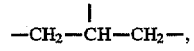

or,
when Y is OH and a is 4,
X is

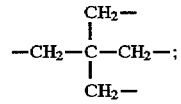

in the compound of the formula II, the radicals Z are hydrogen or a group of the formula

k is the number 1, and
$R_{11}$ is $C_1$–$C_{20}$alkyl or $C_8$–$C_{20}$alkenyl, with the proviso that the compound of the formula II comprises a group

and
in the compound of the formula III,
$R_{12}$ is tert-butyl,
$R_{15}$ is $C_1$–$C_4$alkyl and is bonded in the ortho-position relative to the OH group,
s is the number 1,
Q is —$C_mH_{2m}$— and is bonded in the para-position relative to the OH group, where,
m is the number 2,
n is 1 and
$R_{17}$ is $C_1$–$C_4$alkyl.

6. A composition as claimed in claim 1 in which in component β), in the compound of formula III,
$R_{12}$ is $C_1$–$C_4$alkyl or cyclohexyl,
$R_{15}$ is $C_1$–$C_4$alkyl or cyclohexyl and is bonded in the ortho-position relative to the OH group,
s is the number 1,
Q is —$C_mH_{2m}$— and is bonded in the para-position relative to the OH group, where
m is an integer ranging from 0 to 3, and
n is an integer 1, 2 or 4, where,
when n is 1,
$R_{17}$ is hydrogen, $C_1$–$C_{10}$alkyl, cyclohexyl, $C_2$–$C_{18}$alkenyl or

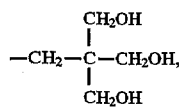

or,
when n is 2,
$R_{17}$ is

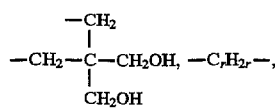

in which
p is an integer ranging from 2 to 4,
q is an integer ranging from 2 to 10,
r is an integer ranging from 2 to 6,
$T_4$ is sulfur, or,
when n is 4, $R_{17}$ is

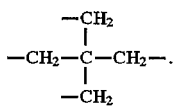

7. A composition as claimed in claim 1 in which in component β), in the compound of formula III, $R_{12}$ is tert-butyl, $R_{15}$ is $C_1$–$C_4$alkyl and is bonded in the ortho position relative to the OH group, s is the number 1, Q is —$C_mH_{2m}$— and is bonded in the para-position relative to the OH group, in which m is the number 2, and n is an integer 1, 2 or 4, where when n is 1, $R_{17}$ is $C_1$–$C_4$alkyl, or, when n is 2, $R_{17}$ is —[(CH$_2$)$_p$O]$_q$—(CH$_2$)$_p$— or —CH$_2$CH$_2$—T$_4$—CH$_2$CH$_2$—, in which p is the number 2, q is the number 2, and $T_4$ is sulfur, or, when n is 4, $R_{17}$ is

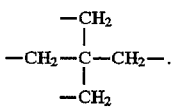

8. A composition as claimed in claim 1 in which in component β), the compound of formula I is pentaerythritol, thiodiethylene glycol, 1,4-butanediol, 1,2-propanediol, diethylene glycol, triethylene glycol or glycerol; the compound of formula II is sunflower oil, coconut fat, rapeseed oil, maize germ oil, safflower oil, olive oil, groundnut oil or Radiamuls; and the compound of formula III is methyl 3-(3',5'-di-tert-butyl-4'-hydroxyphenyl)propionate or methyl 3-(3'-tert-butyl-4'-hydroxy-5'methylphenyl)propionate.

9. A composition as claimed in claim 1 in which in component β), the amount by weight of active group E-2

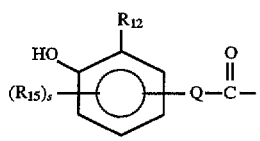

is 30 to 80% by weight.

10. A composition as claimed in claim 1 in which in component β), the first components a) and b) are reacted with each other and the resulting intermediate is subsequently reacted with component c).

11. A composition as claimed in claim 1, in which component α) is a lubricant, a hydraulic fluid, a metal-working fluid or a synthetic polymer.

12. A composition as claimed in claim 11, in which component α) is a lubricant which is a mineral oil, a synthetic oil or a mixture thereof.

13. A composition as claimed in claim 11, in which component α) is a synthetic polymer.

14. A composition as claimed in claim 13, in which component α) is a polyolefin or a styrene copolymer.

15. A process for stabilising polymers or oils against oxidative, thermal or light-induced degradation, which comprises incorporating a product as claimed in claim 1 into these polymers or oils.

* * * * *